(12) United States Patent
Hane

(10) Patent No.: US 10,670,388 B2
(45) Date of Patent: Jun. 2, 2020

(54) SHAPE SENSOR SYSTEM

(71) Applicant: OLYMPUS CORPORATION, Tokyo (JP)

(72) Inventor: Jun Hane, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 16/178,653

(22) Filed: Nov. 2, 2018

(65) Prior Publication Data

US 2019/0072378 A1 Mar. 7, 2019

Related U.S. Application Data

(63) Continuation of application No. PCT/JP2016/063666, filed on May 6, 2016.

(51) Int. Cl.
*G01B 11/16* (2006.01)
*A61B 1/00* (2006.01)
(Continued)

(52) U.S. Cl.
CPC .......... *G01B 11/16* (2013.01); *A61B 1/00002* (2013.01); *A61B 1/00006* (2013.01);
(Continued)

(58) Field of Classification Search
CPC ....... G01B 11/16; G01B 11/255; G01B 11/18; G01B 11/24; A61B 1/00002; A61B 1/005;
(Continued)

(56) References Cited

U.S. PATENT DOCUMENTS

| 6,023,325 A | 2/2000 | Sahlgren et al. |
| 2002/0088931 A1 | 7/2002 | Danisch et al. |

(Continued)

FOREIGN PATENT DOCUMENTS

| JP | H11-514940 A | 12/1999 |
| JP | 2001-169998 A | 6/2001 |

(Continued)

OTHER PUBLICATIONS

English translation of International Preliminary Report on Patentability dated Nov. 15, 2018 together with the Written Opinion received in related International Application No. PCT/JP2016/063666.
International Search Report dated Aug. 2, 2016 issued in PCT/JP2016/063666.
Japanese Office Action dated Nov. 26, 2019 in Japanese Patent Application No. 2018-515386.

(Continued)

*Primary Examiner* — Tri T Ton
(74) *Attorney, Agent, or Firm* — Scully, Scott, Murphy & Presser, P.C.

(57) ABSTRACT

The shape sensor system of the present invention includes a braided structure in which small diameter bending members including two or more optical fibers, provided with detection target portions, are spirally wound around a core member as an axis in directions opposite to each other, or a braided structure in which three or more small diameter bending members including an optical fiber and a dummy optical fiber or a thin metal wire are braided, a plurality of detection target portions are distributed in the direction around the axis of the core member, the bending directions of the respective bending members are synthesized to detect a bending shape of the probe portion, a function of adjusting the fiber length in a braiding cycle is performed, and position deviation does not occur.

14 Claims, 20 Drawing Sheets

(51) Int. Cl.
*A61B 1/005* (2006.01)
*G01B 11/255* (2006.01)
*G01D 5/26* (2006.01)
*G02B 6/06* (2006.01)

(52) U.S. Cl.
CPC ............ *A61B 1/0055* (2013.01); *G01B 11/18* (2013.01); *G01B 11/255* (2013.01); *G01D 5/268* (2013.01); *G02B 6/06* (2013.01); *A61B 1/005* (2013.01)

(58) Field of Classification Search
CPC ..... A61B 1/00; A61B 1/00006; A61B 1/0055; G01D 5/268; G02B 6/06
USPC .................................................. 356/600–640
See application file for complete search history.

(56) References Cited

U.S. PATENT DOCUMENTS

| | | | |
|---|---|---|---|
| 2007/0116415 | A1 | 5/2007 | Kobayashi |
| 2011/0205526 | A1 | 8/2011 | Brown et al. |

FOREIGN PATENT DOCUMENTS

| | | |
|---|---|---|
| JP | 2004-517331 A | 6/2004 |
| JP | 2007-044412 A | 2/2007 |
| JP | 2007-143600 A | 6/2007 |
| JP | 2013-178210 A | 9/2013 |

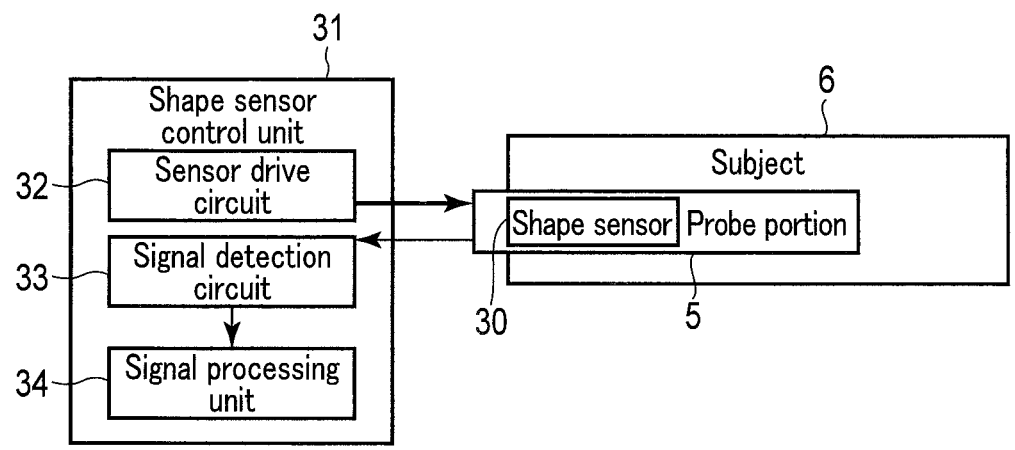
F I G. 1A
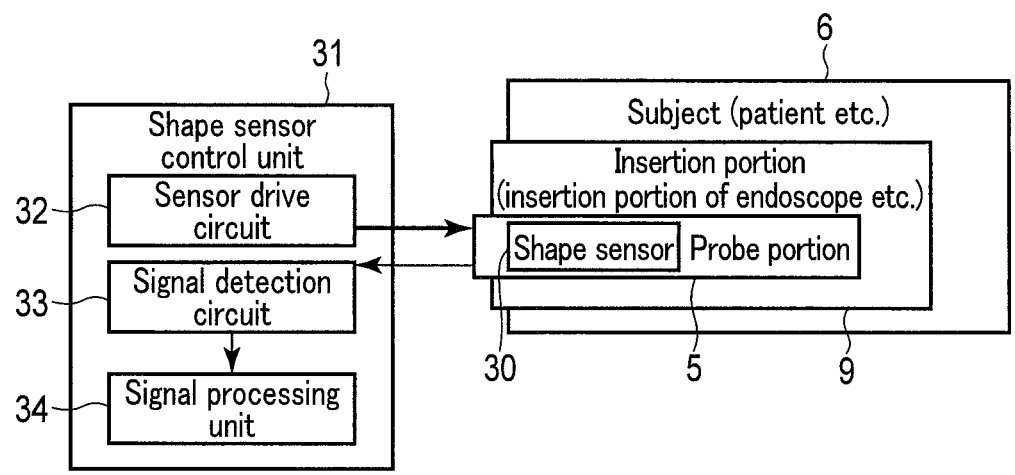
F I G. 1B

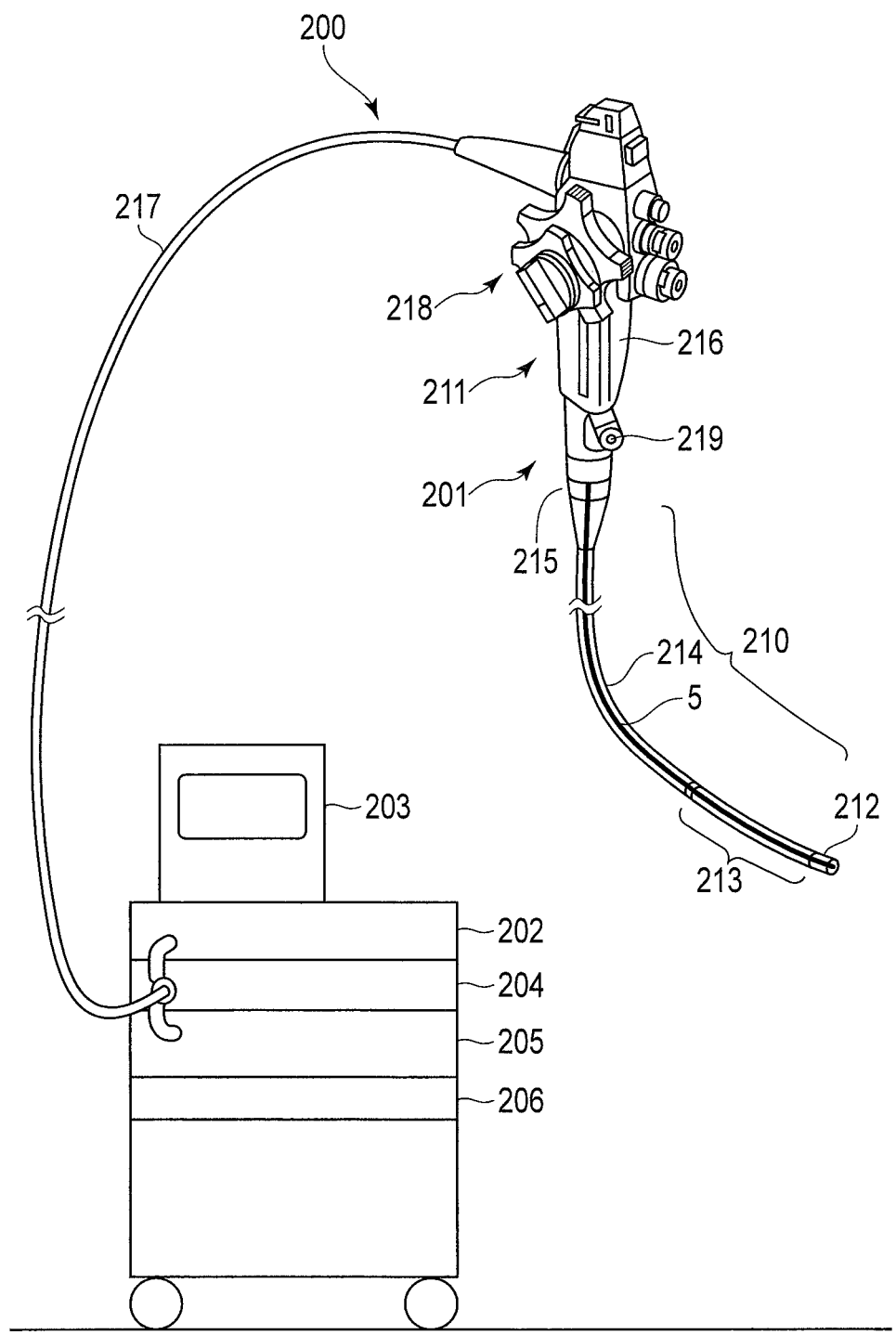
F I G. 2

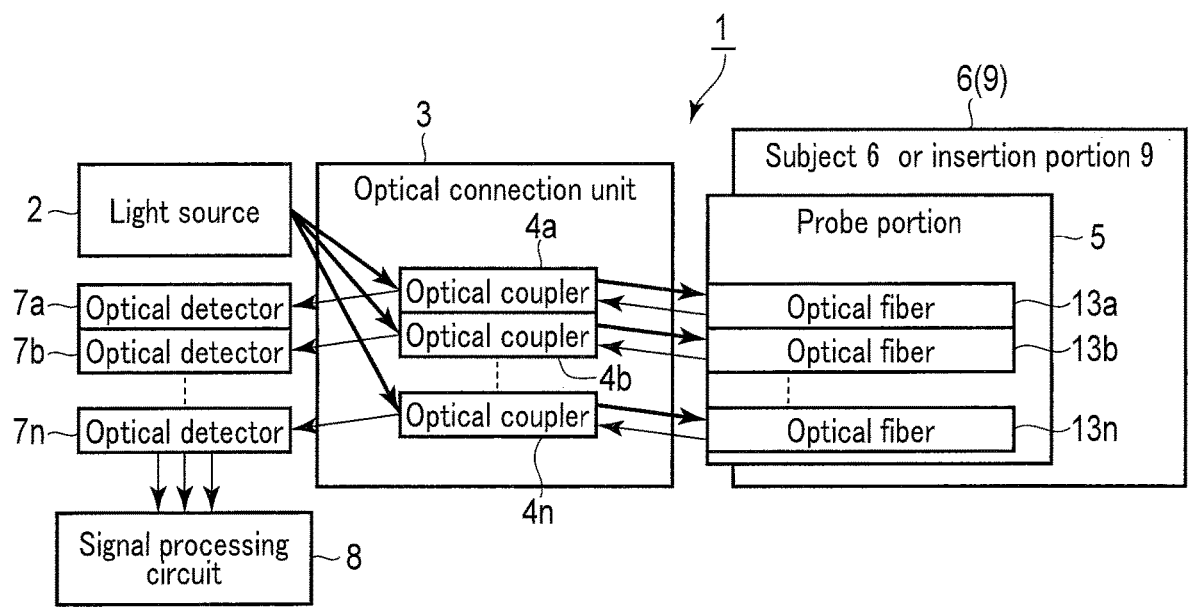
F I G. 10
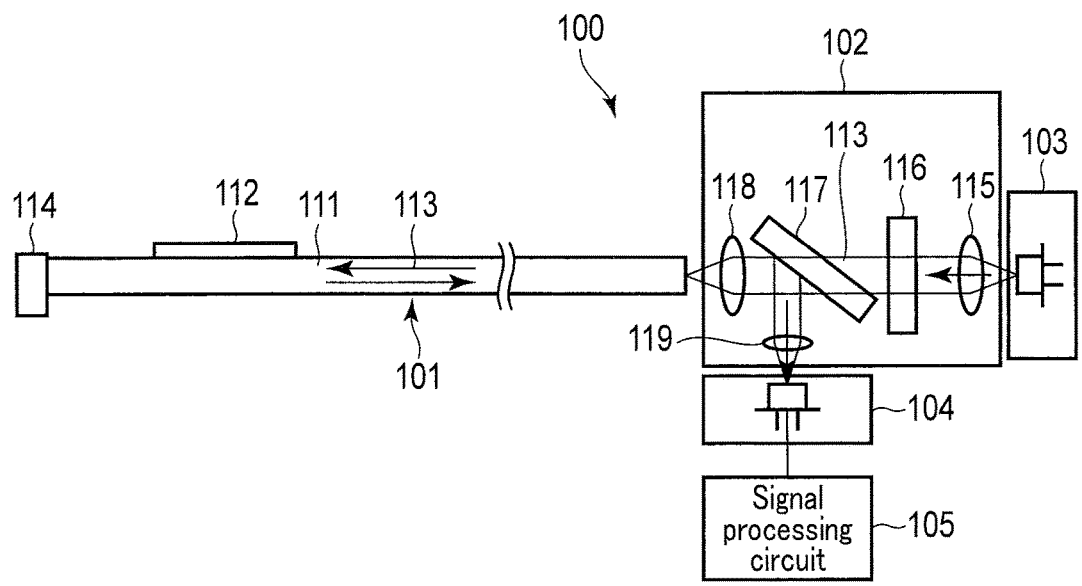
F I G. 11A

Amount of transmitted light: large

Amount of transmitted light: medium

Amount of transmitted light: small

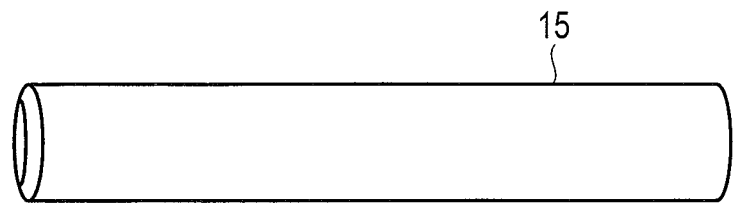
F I G. 12
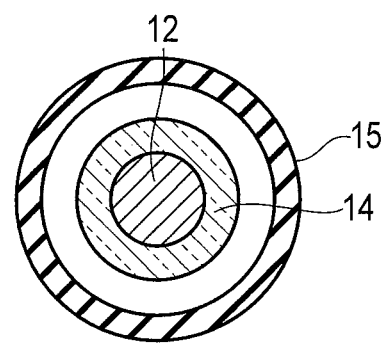
F I G. 13A
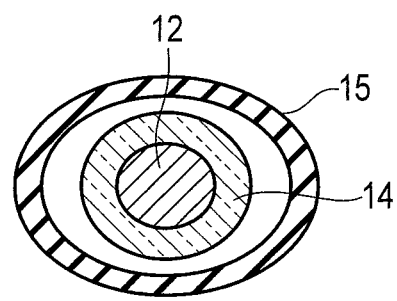
F I G. 13B

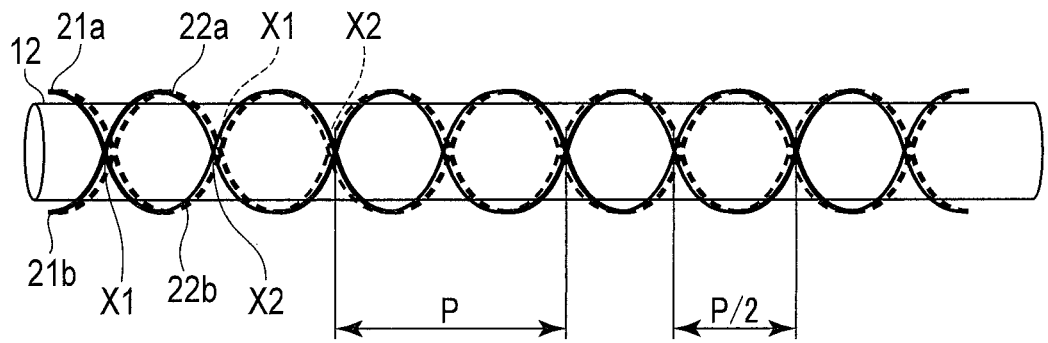
F I G. 14A
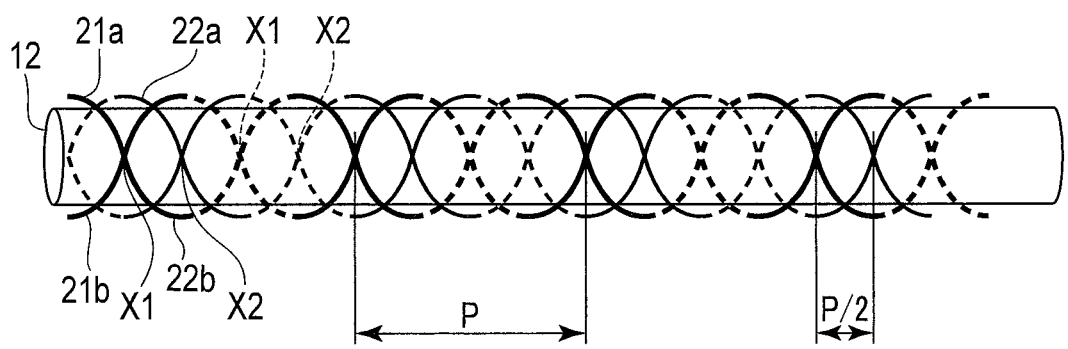
F I G. 14B
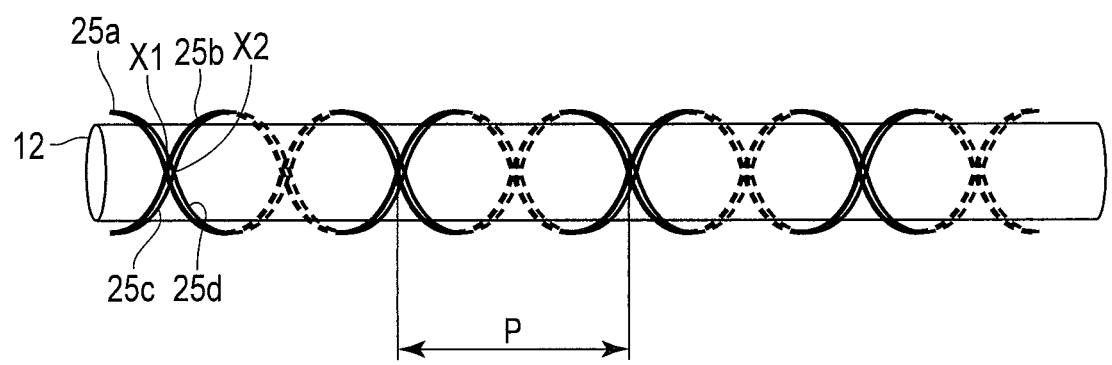
F I G. 14C

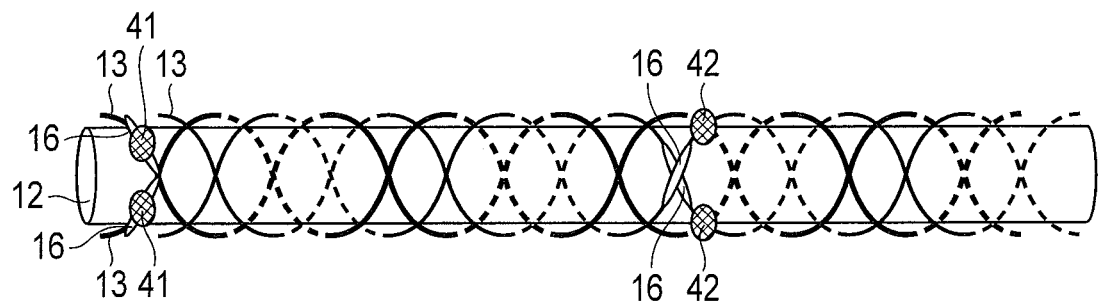
F I G. 16A
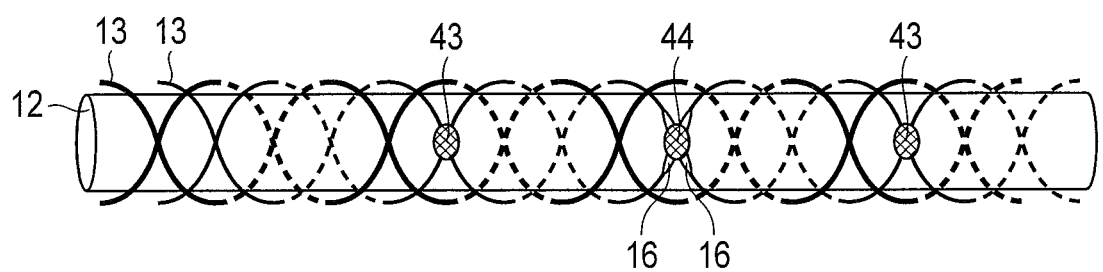
F I G. 16B
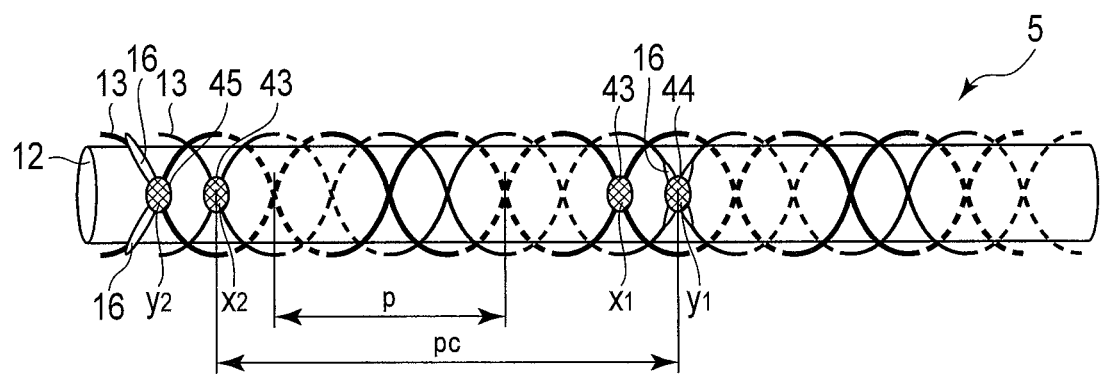
F I G. 17A

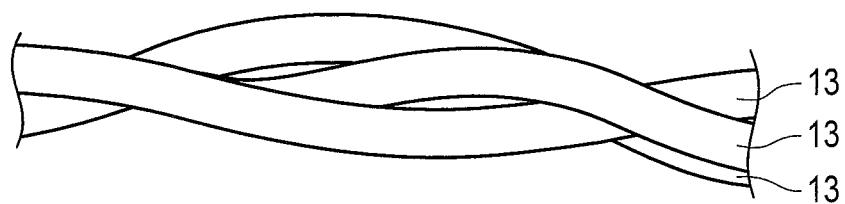
F I G. 21A
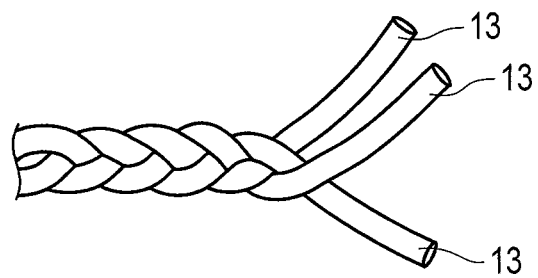
F I G. 21B
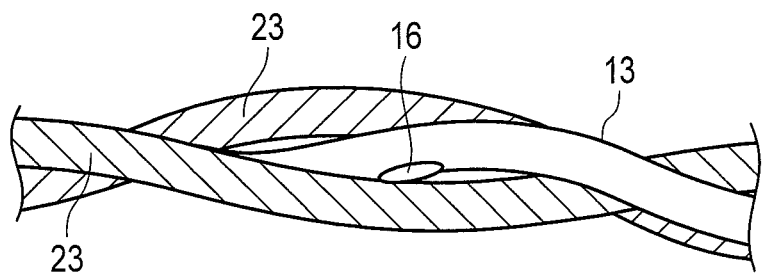
F I G. 22

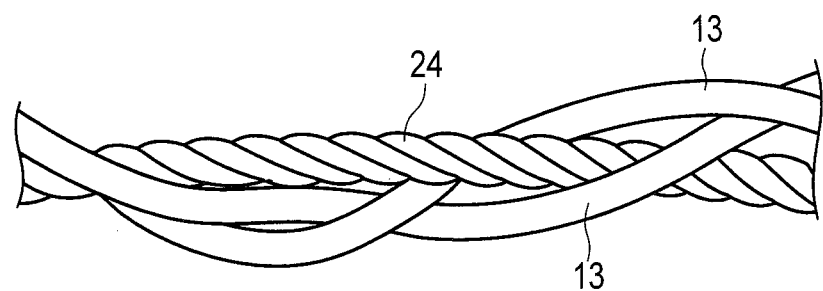
F I G. 23
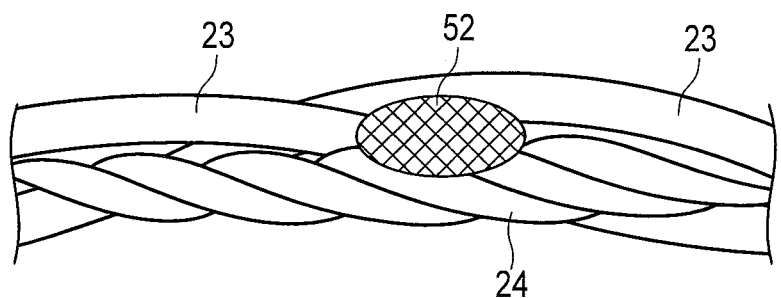
F I G. 24

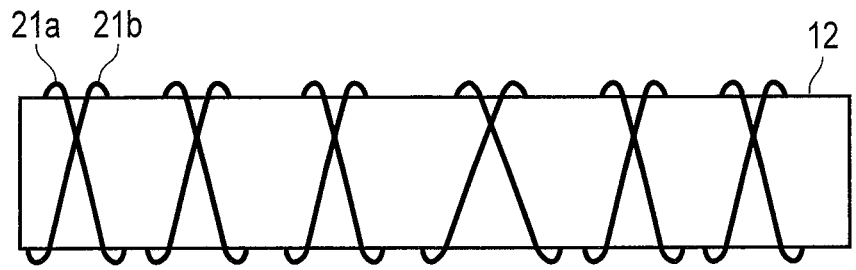
F I G. 25
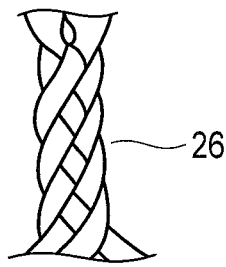
F I G. 26A
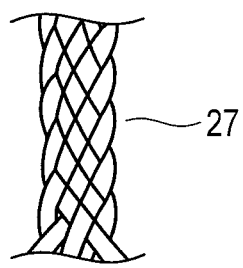
F I G. 26B

SHAPE SENSOR SYSTEM

CROSS-REFERENCE TO RELATED APPLICATIONS

This application is a Continuation Application of PCT Application No. PCT/JP2016/063666, filed May 6, 2016, the entire contents of which are incorporated herein by reference.

BACKGROUND OF THE INVENTION

1. Field of the Invention

The present invention relates to a shape sensor system which is to be attached to a subject whose shape changes, and detects a state of the subject.

2. Description of the Related Art

For a tubular insertion system with a flexible insertion portion known for endoscopes or the like, a shape sensor is incorporated in the insertion portion to detect a changing shape of the insertion portion. As the shape sensor, for example, Jpn. Pat. Appln. KOKAI Publication No. 2007-143600 discloses a shape detection probe using an optical fiber provided with a light modulation unit as a detection target portion. In the shape detection probe, the optical fiber is assembled so as to bend integrally with the insertion portion of an endoscope. This optical fiber transmits light beams having different wavelength components. The light modulation unit modulates the intensity etc. of the wavelength component of the light beam to be transmitted. Based on the intensity etc. of the wavelength component before and after the modulation detected by the light modulation unit, the shape detecting probe detects the shape of the optical fiber at the place where the light modulation unit is disposed, that is, the shape of the endoscope bending along with the optical fiber.

In addition, Jpn. PCT National Publication No. 2004-517331 proposes a structural example in which a first fiber set spirally wound in a single rotational direction and a second fiber set spirally wound in the opposite rotational direction are braided together.

BRIEF SUMMARY OF THE INVENTION

According to an embodiment of the present invention, there is provided a shape sensor system to detect a bending state ora bending shape of a subject, comprising a shape sensor, the shape sensor including: a probe portion that has a long shape and that is bendable in accordance with a shape of a target portion of the subject; a sensor drive circuit to detect a shape of the probe portion; a signal detection circuit to detect signals associated with a shape of the subject; and a signal processor to estimate the shape of the subject from the detected signals, the probe portion including: a core member having a high rigidity and extending along a longitudinal direction of the probe portion; a plurality of small diameter bending members braided around the core member and including one or more small diameter bending probe elements provided with one or more detection target portions from which information is detected to detect the shape of the probe portion, the small diameter bending members including at least two bundles that are divided into two, wherein one bundle is spirally wound around the core member clockwise about a longitudinal direction of the core member, the other bundle is spirally wound around the core member counterclockwise in the longitudinal direction of the core member, and the two bundles intersect each other at a plurality of portions and form a braided structure that holds the detection target portions so as not to be rotated around the longitudinal direction.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1A is a conceptual configuration diagram of a shape sensor system as a whole according to a first embodiment, showing an example in which the shape sensor system is directly attached to a subject.

FIG. 1B is a conceptual configuration diagram of the shape sensor system as a whole according to the first embodiment, showing an example in which the probe portion is incorporated into an insertion device which is to be inserted into a subject.

FIG. 2 is a schematic view showing an appearance of an endoscope system (tubular insertion system).

FIG. 10 is a diagram showing a configuration example of a shape sensor system having a plurality of optical fibers.

FIG. 11A is a view showing a basic configuration of a shape sensor system.

FIG. 12 is a view showing an outer shape of the sheath member.

FIG. 13A is a cross-sectional view of a probe portion in a linear state.

FIG. 13B is a cross-sectional view of a probe portion in a bending state.

FIG. 14A is a view showing a first example of a braided structure with a core member.

FIG. 14B is a view showing a second example of a braided structure with a core member.

FIG. 14C is a view showing a third example of a braided structure with a core member.

FIG. 16A is a view showing a first structural example for holding an optical fiber.

FIG. 16B is a view showing a second structural example for holding an optical fiber.

FIG. 17A is a view showing a structural example in which a holding portion that bonds optical fibers to a core member is provided for every two bundles in a cycle longer than a pitch p.

FIG. 21A is a view showing a structural example of a triple braid in a shape sensor system according to a second embodiment.

FIG. 21B is a schematic view showing a triple braid of strings.

FIG. 22 is a view showing a structural example of a triple braid of small diameter bending members, including dummy optical fibers, according to a first modification.

FIG. 23 is a view showing a structural example of a triple braid of small diameter bending members, including a metal strand, according to a second modification.

FIG. 24 is a view showing a state in which the vicinity of a detection target portion is fixed by adhesion in the second modification.

FIG. 25 is a view showing a structural example of a triple braid with flat knots in which two small diameter bending members are tied to a core member with flat knots.

FIG. 26A is a view showing a structural example of a quadruple braid.

FIG. 26B is a view showing a structural example of a sextuple braid.

DETAILED DESCRIPTION OF THE INVENTION

Figure 1C:
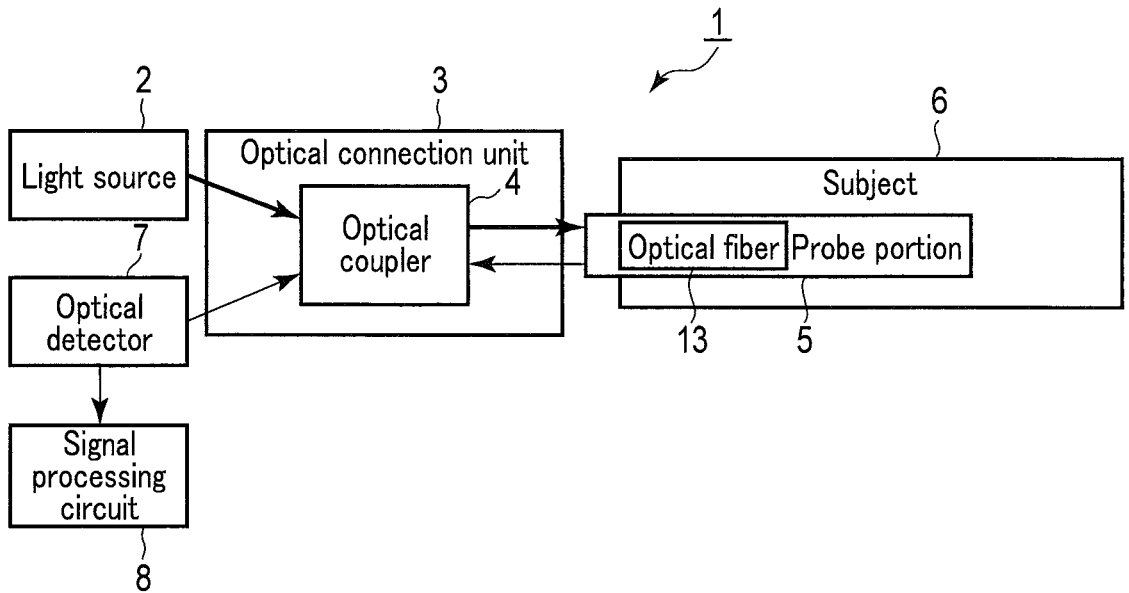
FIG. 1C is a conceptual configuration diagram of a shape sensor system in which a shape sensor shown in FIG. 1A is attached to an optical fiber.

Hereinafter, embodiments of the present invention will be described in detail with reference to the drawings.

Fiber sensors, strain sensors, and the like are available as shape sensors for detecting a long shape. Of the shape sensors, the fiber sensor is small in diameter and capable of detecting a bending at multiple points (a plurality of points). In addition, the fiber sensor requires no power supply except for supply of light, and is hardly affected by electromagnetic noise. For these reasons, the fiber sensor is effective for detecting the shape of a subject having an elongated shape.

In the following, the fiber sensor will be mainly described as an example of the shape sensors. However, any type of shape sensor other than the fiber sensor may be used, as long as it is formed of an elongated probe portion that can detect the shape of a subject.

A shape sensor system 1 is attached to a long and flexible subject along its longitudinal direction, and detects a changing shape of a tubular member. The subject may be an insertion device (or a tubular insertion system) to be inserted in a lumen for observation and treatment, such as repair, medical treatment and collection, typified by a medical endoscope (for upper gastrointestinal tract, colon, ultrasound, etc.), an industrial endoscope, a rigid endoscope having a bending mechanism in a part, and a catheter. Besides, a manipulator having a joint (e.g., a robot arm), a part of a human or animal having a joint, etc. can be applied as a subject.

In the following embodiment, an insertion device is taken as an example of a subject, to which a probe portion having fiber sensors are attached. Specifically, an insertion portion of an endoscope will be described as an example of the subject. Furthermore, it is assumed that the longitudinal direction of a probe portion (described later) and the longitudinal direction of a core member (described later) coincide with each other.

As shown in FIG. 2, an endoscope system (tubular insertion system) 200 includes an endoscope 201 that images an observation target with an imaging unit provided at a distal end of the insertion portion, an image processing device 202 (video processor) that image-processes an imaged result, and a monitor 203, which is a display unit that is connected to the image processing device 202 and displays the observed and image-processed observation image.

The endoscope system 200 includes a light source device 204, a light emission detection device 205, and a control device 206. The light source device 204 emits illumination light toward the endoscope 201. The light emission detection device 205 emits light for detection of a shape sensor (to be described later), which is different from the illumination light, and detects this light. The control device 206 controls the endoscope system 200. Here, the observation target is an affected part, a disease part, or the like in a subject body (for example, a body cavity (lumen)).

The endoscope 201 is provided with an elongated insertion portion 210 and an operation unit 211 connected to a proximal end portion of the insertion portion 210. The endoscope 201 is a tubular insertion device for inserting the tubular insertion portion 210 into a body cavity. The insertion portion 210 has a distal end rigid portion 212, a bending portion 213, and a flexible tube portion 214, which are arranged in this order from the distal end side to the proximal end side of the insertion portion 210. The proximal end portion of the distal end rigid portion 212 is connected to the distal end portion of the bending portion 213 and the proximal end portion of the bending portion 213 is connected to the distal end portion of the flexible tube portion 214.

The distal end rigid portion 212 is the distal end portion of the insertion portion 210 and the distal end portion of the endoscope 201. The distal end rigid portion 212 is hard, and the imaging portion is disposed therein. The bending portion 213 is bent in a desired direction by operating the bending operation portion 218 including two knobs. The bending operation portion 218 bends the bending portion 213 to change the position and direction of the distal end rigid portion 212, captures the observation target in an observation field of view, and illuminates the observation target with the illumination light. The bending portion 213 is formed by connecting node rings (not shown) along a longitudinal axis direction of the insertion portion 210.

The flexible tube portion 214 has desired flexibility and is bent by external force. The flexible tube portion 214 is a tubular member extending from a main body portion 215 of the operation unit 211. Because of the flexibility of the flexible tube portion 214, the bending portion 213 can be inserted into a lumen, such as the gastrointestinal tract, the bronchi, the urinary organ or the like of a patient as a subject body, while bending or twisting the bending portion 213.

The operation unit 211 includes a main body portion 215 from which the flexible tube portion 214 extends, a grip portion 216, and a universal cord 217 connected to the grip portion 216. The grip portion 216 is connected to the proximal end portion of the main body portion 215 and gripped by an operator (such as a doctor) who is operating the endoscope 201.

Figure 3A:
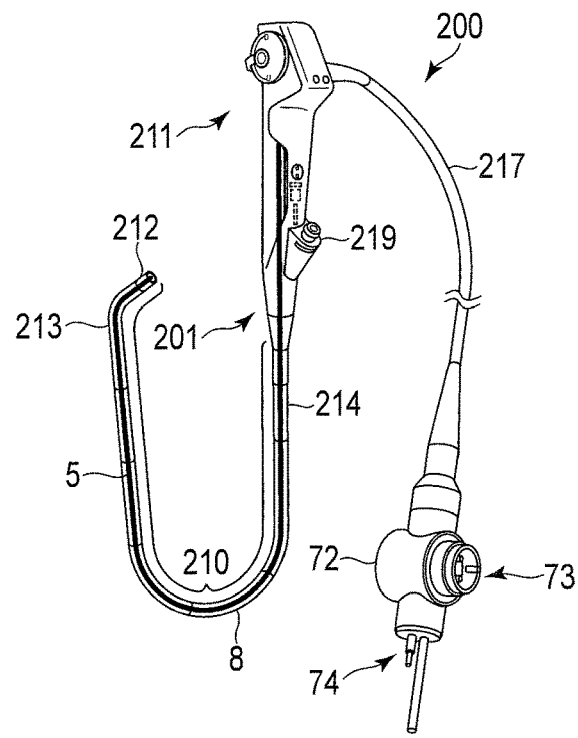
FIG. 3A is a schematic view showing a structural example in which an insertion portion, a grip portion, and a universal cord of the endoscope are integrated.
Figure 3B:
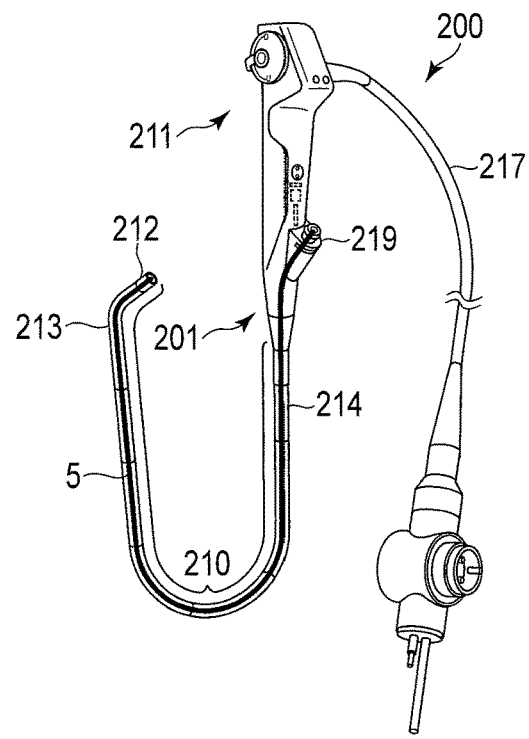
FIG. 3B is a schematic view showing a structural example in which a detachable type probe portion is inserted through a forceps channel and attached to the endoscope.

FIG. 3A shows a structure in which the insertion portion of the endoscope, the grip portion, and the universal cord are integrated. As a specific arrangement of the probe portion 5 as a shape sensor, as shown in FIG. 3A, an incorporated-type flexible tube portion 214 incorporating the probe portion 5 may be adopted. Further, as shown in FIG. 3B, the probe portion 5 may be attached to and detached from the endoscope 201 as necessary through a forceps channel or the like. A signal detection circuit detects signals associated with a sensor drive circuit (not shown) and a subject shape. The signal detection circuit may be disposed on the probe portion side or on the endoscope main body side.

Figure 4:
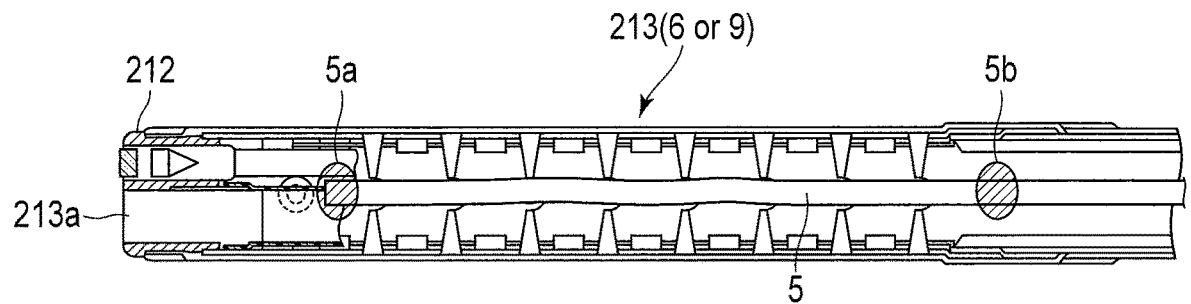
FIG. 4 is an enlarged longitudinal sectional view showing a configuration in which a probe portion is incorporated in an insertion portion.
Figure 5:
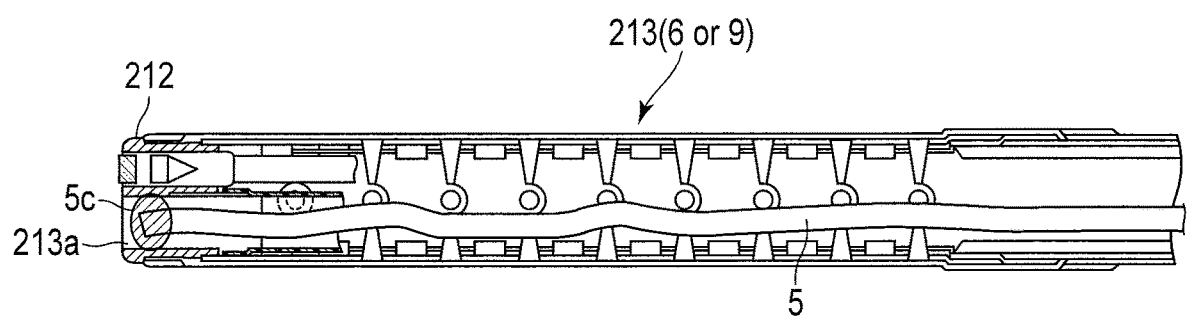
FIG. 5 is an enlarged longitudinal sectional view showing a configuration in which a probe portion is detachably attached to an endoscope through a forceps channel.
Figure 6:
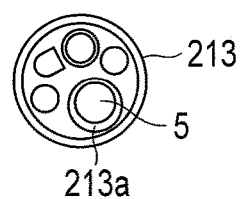
FIG. 6 is an enlarged transversal sectional view showing a configuration in which a probe portion is detachably attached to an endoscope through a forceps channel.

FIG. 4 and FIG. 5 show enlarged sections of structures in which the detachable type probe portion 5 is incorporated into the bending portion 213, which is a subject 6 or an insertion portion 9. FIG. 6 is a view showing a configuration of the distal end rigid portion 212 of the bending portion 213 viewed from the front. If the probe portion 5 is detachable, if necessary, fixtures and fixing mechanisms may be used as appropriate.

FIG. 4 and FIG. 5 show fixation candidate positions 5a, 5b, and 5c for fixing the probe portion 5 in the bending portion 213 when the probe portion 5 is incorporated in the bending portion 213. Whether or not to fix the probe portion 5 to the respective fixation candidate positions 5a, 5b, and 5c is determined depending on whether an optimum result can be obtained in accordance with the mechanical characteristics and the shape detection performance of the probe portion 5. For example, the configuration of fixing the probe portion 5 in the fixation candidate position 5a on the distal end side and the fixation candidate position 5b on the rear end side in the bending portion 213 is effective from the viewpoint of ensuring stability and ease of manufacturing in the incorporated type shown in FIG. 4.

Further, in the detachable type probe portion 5 as shown in FIG. 5, it is effective to fix the tip of the probe portion 5 to the distal end side in the bending portion 213.

Adding fixation other than those described above as appropriate is an effective method from the viewpoint of manufacturing when stability improvement is required. Regarding fixation, in an incorporated type, a permanent and stable method such as adhesion, tightening, or screwing is desirable. On the other hand, in the detachable type probe portion 5, for example, a spacer may be fit in a guide hole such as a forceps channel, or a balloon may be inflated in the guide hole so that the probe portion 5 cannot move.

First, the basic configuration of the shape sensor system will be explained.

A shape sensor system 100 shown in FIG. 11A includes a probe portion 101 having an optical fiber, an optical connection unit 102, a light source 103, an optical detector 104, and a signal processing circuit 105.

The probe portion 101 is provided with a detection target portion (bending detection portion) 112 for detecting a bending state on a peripheral surface of an optical fiber 111 having at least the same length as the insertion portion 210. A reflection member 114 is arranged at the tip of the probe portion 101. The light source 103 is, for example, an LED light source or a laser light source that emits a light beam as detection light having desired wavelength characteristics. As the optical detector 104, a light receiving element such as a photodiode can be used. The optical detector 104 photoelectrically converts the received detection light and outputs an electric signal representing an amount of light.

An emission path side of the optical connection unit 102 includes a collimator lens 115, a polarization filter or λ/4 wave plate 116, a polarization beam splitter 117, and an objective lens 118. An incident path side of the optical connection unit 102 includes the objective lens 118 and the polarization beam splitter 117, which are used in common with the emission path side, and a condenser lens 119. The signal processing circuit 105 detects the bending amount from the light beam returned by the reflection of the reflection member 114 based on a fluctuation of the light amount loss in the bending detection portion 112.

Figure 11B:
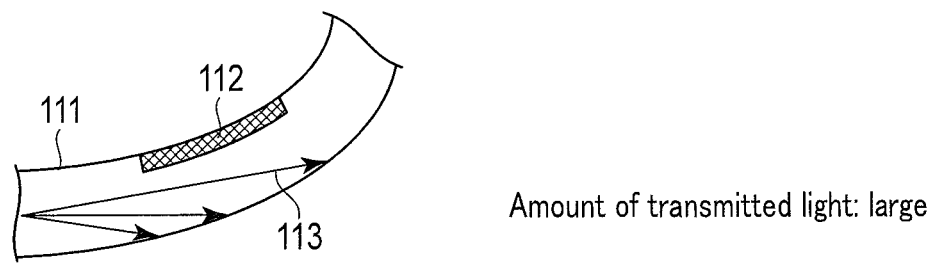
FIG. 11B is a view for explaining an incidence of a light beam to a bending detection portion in an upwardly bent optical fiber.
Figure 11C:
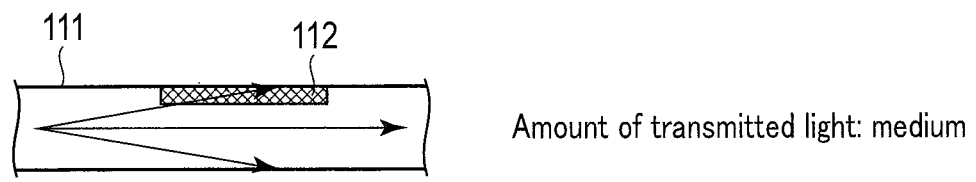
FIG. 11C is a view for explaining an incidence of a light beam to a bending detection portion in a straight optical fiber.
Figure 11D:
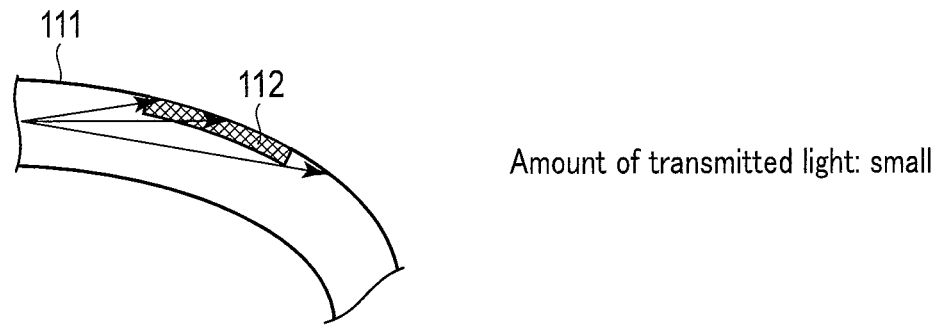
FIG. 11D is a view for explaining an incidence of a light beam to a bending detection portion in a downwardly bent optical fiber.

As shown in FIGS. 11B, 11C, and 11D, when one detection target portion 112 is provided in the optical fiber 111, the light amount of the light beam (laser light) may be lost by the detection target portion 112, depending on the bending direction.

In the detection target portion 112, a part of the coating and cladding is removed from the peripheral surface of the optical fiber 111, and a light opening is formed so as to expose the core. This light opening portion is filled with an optical characteristic converting member. The optical characteristic conversion member is a light guide loss member (light absorber), a wavelength conversion member (phosphor), or the like for converting the light amount and characteristics of the light beam guided to the optical fiber 111. In the embodiments described below, for example, a light guide loss member is used as the optical characteristic conversion member.

In the shape sensor system 100, a light beam 113 emitted from the light source 103 is guided to the optical fiber 111 via the optical connection unit 102. Apart of the light beam 113 is absorbed by the optical characteristic conversion member of the detection target portion 112 on the way and the light amount is lost. The amount of light guide loss varies depending on the bending amount and the bending direction of the optical fiber 111.

For example, as shown in FIG. 11C, even though the optical fiber 111 is in a linear state, a part of the light beam to be guided is incident on the detection target portion 112, and a certain amount of light is lost. Based on this amount of light loss as a reference, the optical fiber 111 is determined to be in a linear state.

As shown in FIG. 11B, if the optical fiber 111 is in a bending state in which the detection target portion 112 is disposed on the inner peripheral side (inner side), the light beam incident on the characteristic conversion member is small, and the light guide loss amount is smaller than the reference light guide loss amount. On the contrary, as shown in FIG. 11D, if the optical fiber 111 is in a bending state in which the detection target portion 112 is disposed on the outer peripheral side (outer side), the light beam incident on the characteristic conversion member is large, and the light guide loss amount is larger than the reference light guide loss amount.

The change in the light guide loss amount is reflected in the detected light amount received by the optical detector 104, that is, the output signal. Therefore, the signal processing circuit 105 can estimate the bending shape (bending direction and bending angle) of the place where the detection target portion 112 is arranged, based on the output signal of the optical detector 104.

As described above, in the shape sensor system 100, the optical detector 104 detects a light amount modulation by the detection target portion 112 of the optical fiber 111, and the bending amount (bend degree) can be detected from the detected signal value. Further, by distributing a plurality of detection target portions 112 in the direction around the axis of the optical fiber 111 and combining the respective bending directions, the bending shape of the probe portion 101 can be detected, and accordingly the bending shape of the subject can be recognized. By attaching this shape sensor system 100 to the insertion portion of the endoscope, it is possible to recognize a physical state such as the bending shape of the insertion portion, so that the insertion portion can be inserted into the human body for observation, diagnosis, treatment and the like.

First Embodiment

Next, the shape sensor system according to the first embodiment will be described with reference to FIGS. 1A to 1D and FIG. 7.

Figure 1D:
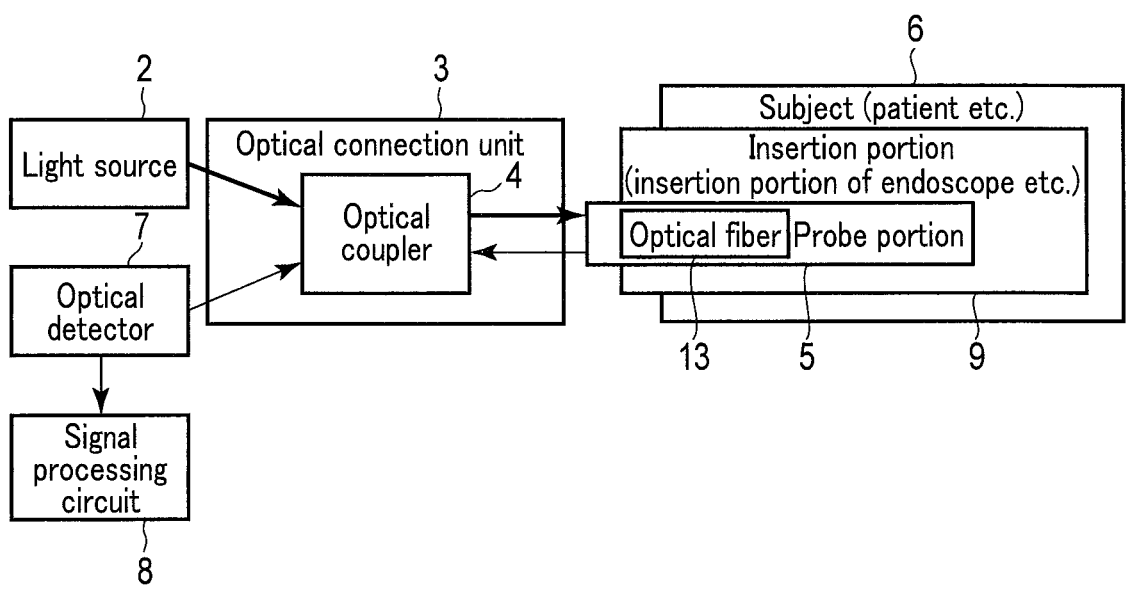
FIG. 1D is a conceptual configuration diagram of a shape sensor system in which a shape sensor shown in FIG. 1B is attached to an optical fiber.
Figure 7:
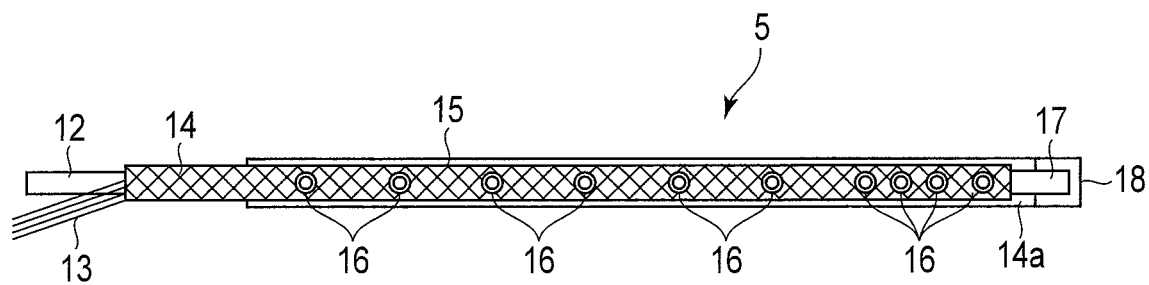
FIG. 7 is a view showing a configuration of a probe portion.

FIG. 1A shows a conceptual configuration of a shape sensor system as a whole, showing an example in which the shape sensor system is directly attached to a subject. FIG. 1B shows a conceptual configuration of the shape sensor system as a whole, showing an example in which the probe portion is incorporated into an insertion device (or an insertion portion) to be inserted into a subject. FIG. 1C shows a conceptual configuration of a shape sensor system in which the shape sensor shown in FIG. 1A is attached to an optical fiber in the system. FIG. 1D shows a conceptual configuration of a shape sensor system in which the shape sensor shown in FIG. 1B is attached to an optical fiber in the system. FIG. 7 is a diagram showing the configuration of the probe portion.

As shown in FIG. 1A, the shape sensor system 1 according to the present embodiment includes a shape sensor control unit 31 and a probe portion 5. The shape sensor control unit 31 includes a sensor drive circuit 32, a signal detection circuit 33, and a signal processor 34. The probe portion 5 is composed of a braided structure formed of small diameter bending members with a core member (to be described later) and includes shape sensors 30. In this configuration, the sensor drive circuit 32, the signal detection circuit 33, and the signal processor 34 are equivalent to the light source 103, the optical detector 104, and the signal processing circuit 105 described above with reference to FIG. 11A.

The sensor drive circuit 32 performs sensor drive necessary for acquiring shape signals of the shape sensors 30, which are detection target portions, provided in the probe portion 5, for example, performs control of power supply, supply waveform of the power supply, supply timing, supply target, etc. The signal detection circuit 33 individually detects signals from the shape sensors 30 provided in the probe portion 5 or detects a plurality of signals at the same time. In the signal processor 34, signals of individual shape sensors 30 are separated from detection signals as necessary. After this separation, the amount of bending at each shape sensor 30 is calculated, and the shape of the probe portion 5 is further calculated. The configuration shown in FIG. 1A and the configuration shown in FIG. 1B are different in usage pattern: in the configuration shown in FIG. 1A, the probe portion 5 is directly attached to the subject 6; and in the configuration shown in FIG. 1B, the insertion portion 9 of the endoscope as an insertion device, incorporating the probe portion 5, is inserted into subject 6. The probe portion 5 in FIGS. 1A and 1B has the same configuration. The sensor drive circuit, the signal detection circuit, and the signal processor are all mounted on either the operation unit 211 of the endoscope system or the main body side shown in FIG. 2. Alternatively, they are mounted separately on either of the operation unit 211 or the main body side.

The shape sensor system 1 of the present embodiment uses fiber sensors as a shape sensor. The shape sensor system 1 is composed of a light source 2, an optical connection unit 3 on which an optical coupler 4 is mounted, a probe portion 5 including an optical fiber 13 with a core member (to be described later), an optical detector 7, and a signal processing circuit 8. In this configuration, the light source 2, the optical detector 7, and the signal processing circuit 8 are equivalent to the light source 103, the optical detector 104, and the signal processing circuit 105 described above, and a detailed description thereof will be omitted. The difference between the configuration shown in FIG. 1C and the configuration shown in FIG. 1D is the same as the difference between FIG. 1A and FIG. 1B. In the configuration shown in FIG. 1C, the probe portion 5 is directly attached to the subject 6; and in the configuration shown in FIG. 1D, the insertion portion 9 of the endoscope as an insertion device, incorporating the probe portion 5, is inserted into subject 6. The probe portion 5 in FIGS. 1C and 1D has the same configuration.

The optical connection unit 3 is equipped with the optical coupler 4 having a known structure. The optical connection unit 3 performs light guiding, branching, and multiplexing so as to optically transmit the light beam emitted from the light source 2 to the probe portion 5 and to transmit the light beam reflected from the tip of the probe portion 5 to the optical detector 7. In the present embodiment, the optical coupler 4 is used; however, a configuration using the polarization beam splitter 117 described above may be used. In addition, the light source 2, the optical connection unit 3, the optical detector, and the signal processing circuit 8 are all mounted on either the operation unit 211 of the endoscope system or the main body side shown in FIG. 2. Alternatively, they are mounted separately on either of the operation unit 211 or the main body side.

As shown in FIG. 7, the probe portion 5 is formed of a core member 12, a small diameter bending member (optical fiber) braided portion 14, and a sheath member 15. The small diameter bending member braided portion 14 is formed by spirally winding or braiding two or more bundles of small diameter bending members (e.g., optical fibers) around the core member 12, as will be described later. As an example of a small diameter bending member other than the optical fiber, a shape sensor such as a strain sensor or a wiring material of a shape sensor may be considered.

As the core member 12, a member having a small diameter and being easy to bend is used, and a member having high rigidity against twisting and expansion and contraction is preferable. That is, the core member 12 is flexible and has rigidity against twisting and expansion and contraction. For example, in the case of a metal material, a wire material such as a stainless steel alloy or NiTi, or a stranded wire obtained by twisting these materials can be used. If the core member 12 is made of a resin material, a resin member formed of reinforcing fibers, such as carbon or the like impregnated with a fiber-reinforced resin, may be used. Furthermore, the core member 12 may be a member having not only a solid structure but also a hollow structure obtained by elongating a tube made of a stainless steel alloy into an elongated tube shape by swaging. Furthermore, the core member 12 may have a layer structure in which another member is inserted or filled in the hollow structure and integrated as one.

The optical fiber braided portion 14 of the present embodiment includes a plurality of detection target portions 16 arranged in a row along the longitudinal direction of the core member 12 and fixed to the core member 12. Generally, in order to detect the bending direction, two or more detection target portions 16 are necessary. Furthermore, if the detection range is several hundreds of millimeters or longer, a plurality of detection target portions 16 are required to be arranged in the longitudinal direction. Normally, arrangement of the detection target portions 16 is predetermined in accordance with the shape and detection accuracy that the subject 6 can take; the detection target portions 16 are arranged at intervals of approximately several tens to several hundreds of millimeters.

In the example shown in FIG. 7, the detection target portions 16 are disposed at narrow intervals within the above-mentioned range in the vicinity of the distal end of the probe portion 5, and at wider intervals in the other portions on the proximal end side. This is because a bending mechanism is provided at a distal end portion of the insertion portion where the probe portion 5 is attached, and the bending mechanism is particularly bent; that is, the radius of curvature is small in the distal end portion. Therefore, the vicinity of the distal end portion of the probe portion 5 is a detection range from the distal end where the bending shape must be recognized by the operator, and includes at least a range including a portion of the bending mechanism provided at the distal end of the insertion portion. These detection target portions 16 have a configuration using the above-described light guide loss member or wavelength conversion member or the like for detecting the bending state.

The detection target portions 16 as described above may be disposed on one optical fiber 13 or may be arranged on a plurality of optical fibers 13. In the case of disposing all the detection target portions 16 on one optical fiber 13, reduction in size of the configuration can be realized by reducing the diameter of the probe portion 5 and simplifying the detection system or the like. On the contrary, it becomes difficult to separate and extract the bending information acquired from each of the detection target portions 16, and the cost of the system is increased by the use of the high precision optical detector 7 and the signal processing circuit 8. On the other hand, in the case of distributing the detection target portions 16 on the plurality of optical fibers 13, if the number of optical fibers 13 is increased, the diameter of the probe portion 5 may be increased or a plurality of optical connection units 3 or optical detectors 7 may be required. However, since the number of the detection target portions 16 provided on one optical fiber is reduced, it becomes easy to separate and extract the bending information acquired from the detection target portions 16.

FIG. 10 shows a configuration example of a shape sensor system 1 including a plurality of optical connection units 3 and a plurality of optical detectors 7 when the detection target portions 16 are disposed on the plurality of optical fibers 13 as described above.

The light guide path of the light beam from the light source to the optical detector in the optical fiber 13 provided with the detection target portions 16 may be a known path type, such as a same-path reflection type, a same-path transmission type, or a different-path reflection type. The number of the optical fibers 13 provided with the detection target portions 16 and the type of the light guide path of the light beam applicable to the present embodiment are not particularly limited. FIG. 7 shows the detection target portions 16 arranged in one row. Actually, however, the detection target portions 16 are arranged in rows (not shown) arranged in a circumferential direction at a discretionary angle, for example 90°, so as to detect the bending state of the probe portion 5 in the longitudinal and lateral directions. Of course, the arrangement of the detection target portions 16 is not limited to two rows, and the detection target portions 16 may be arranged in three or more rows along the longitudinal direction of the optical fiber braided portion 14.

Furthermore, a distal end 14a of the optical fiber braided portion 14 is fixed to the distal end side of the core member 12 by using the distal end portion 18. The distal end portion 18 is used for sealing the distal end of the optical fiber braided portion 14 and for fixing the probe portion 5 to the subject 6. When the probe portion 5 is fixed to the insertion portion 9 or the subject 6, the core member 12 is also fixed together by the distal end portion 18. Therefore, the positional shift due to bending is unlikely to occur, and a stable fixed state can be obtained. In some cases, a proximal end side of the optical fiber braided portion 14 may be fixed to the proximal end side opposite to the distal end side of the core member 12.

With reference to FIG. 12, FIG. 13A and FIG. 13B, the sheath member 15 of the probe portion 5 will be described.

FIG. 12 shows an appearance of the sheath member 15, FIG. 13A shows the sectional structure of the probe portion 5 in a linear state, and FIG. 13B shows the sectional structure of the probe portion 5 in a bending state.

The sheath member 15 is formed in a tubular shape so as to enclose a plurality of optical fibers 13 on the outer circumferential surface of the optical fiber braided portion 14. The sheath member 15 is preferably an elastic member that does not hinder the bending of the optical fiber braided portion 14.

The sheath member 15 has a cylindrical shape, and accommodates and protects the optical fiber braided portion 14 therein. The sheath member 15 is provided to prevent the optical fiber braided portion 14 from rotating around the longitudinal axis or moving in the longitudinal direction due to the influence from the outside, or to prevent the optical fiber from moving in the longitudinal direction due to the influence from the outside.

Further, the distal end portion 18 is provided at the tip of the probe portion 5 to appropriately fix the sheath member 15 and the core member 12 as necessary. Furthermore, the distal end portion 18 seals the optical fiber braided portion 14 and includes a function of incorporating the probe portion 5 into the insertion portion 9 in the configuration shown in FIG. 1B. When the probe portion 5 is incorporated into the insertion portion 9, the core member 12 is also fixed to the distal end portion 18, whereby the distal end of the optical fiber braided portion 14 is stably fixed to the insertion portion 9.

Figure 8:
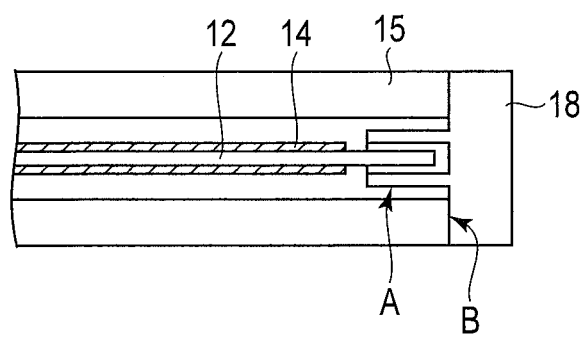
FIG. 8 is a view showing an example of a disposition relationship between a distal end portion and a core member or a sheath member.

FIG. 8 shows a first arrangement example of the distal end portion 18, the core member 12, and the sheath member 15.

In this arrangement example, the core member 12 and the distal end portion 18 are fixed to a fixable portion A between the core member and the distal end portion. Furthermore, if the distal end portion 18 is fixed to the subject (not shown), this fixture is equivalent to fixing the core member to the subject. With this configuration, the stability of the arrangement of the core member 12 relative to the subject is improved.

In this manner, if the sheath member 15 is fixed to the distal end portion 18, the stability of the sheath member 15 relative to the subject also improves. On the other hand, when the sheath member 15 is subject to a large external force or moment from the outside, the sheath member 15 is not fixed to the distal end portion 18. By not fixing the sheath member 15, the influence of a large external force or moment from the outside is less likely to be transmitted to the core member 12 or the optical fiber braided portion 14 which is braided on the core member 12, so that the stability of arrangement of the core member 12 relative to the subject can be improved.

Further, when the core member 12 and the distal end portion 18 are not fixed at the fixable portion A between the core member and the distal end portion, the core member 12 is less affected by the distal end portion 18 and the sheath member 15 at the distal end. If the core member 12 itself is not easily twisted, the stability of arrangement of the core member 12 can be improved. In this case, sealing property of the probe portion 5 of the shape sensor is improved by bonding and fixing the sheath member 15 and the distal end portion 18 without a gap, as in a fixable portion B between the sheath member and the distal end portion.

Figure 9:
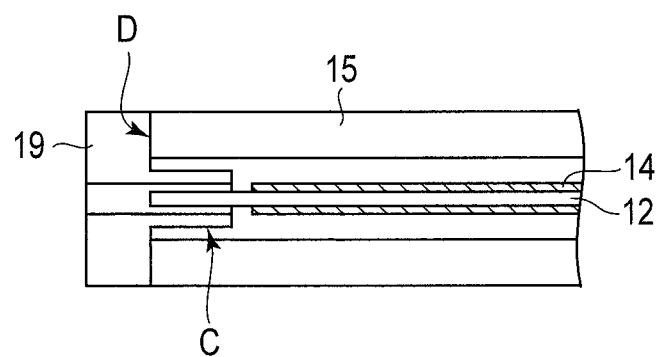
FIG. 9 is a view showing another example of the disposition relationship between the distal end portion and the core member or the sheath member.

FIG. 9 shows a second arrangement example of the rear end portion (proximal end side), the core member 12, and the sheath member 15.

The core member 12 and the rear end portion 19 are fixed in a fixable portion C between the core member and the rear end portion, and only the rear end portion 19 is fixed to the insertion portion 9, which is inserted into the subject 6 (not shown). In this case, this fixture is equivalent to fixing the core member 12 to the insertion portion 9. In this form, the stability of the arrangement of the core member of the shape sensor relative to the insertion portion of the endoscope or the like is improved.

In addition, if the sheath member 15 and the rear end portion 19 are fixed in a fixable portion D between the sheath member and the rear end portion, the stability of the sheath member 15 relative to the insertion portion also improves. On the other hand, when the sheath member 15 is subject to a large external force or moment from the outside, the sheath member 15 is not fixed to the rear end portion 19. By not fixing the sheath member 15, the influence of a large external force or moment from the outside is less likely to be transmitted to the core member 12 or the optical fiber braided portion 14, so that the stability of arrangement of the core member 12 relative to the insertion portion can be improved.

In addition, when the core member 12 and the rear end portion 19 are not fixed at the fixable portion C between the core member and the rear end portion, the core member 12 is less likely to be affected by the rear end portion 19 and the sheath member 15 at the rear end. If the core member 12 itself is not easily twisted the stability of the arrangement of the core member can be improved.

Although the core member 12 extends to a middle of the rear end portion 19, it may penetrate through the rear end portion 19. Further, although the optical fiber braided portion 14 extends from the rear end portion 19 to the distal end side, it is also possible to adjust the inner diameter of the rear end portion 19 appropriately, and then arrange the optical fiber braided portion 14 to extend to a middle of the rear end portion 19 or before the rear end portion 19.

As described above, when the core member 12 has a high torsional rigidity and the influence of a large external force or moment from the outside is relatively small, the core member 12 and the sheath member 15 are fixed at both the distal end portion 18 and the rear end portion 19, so that the torsional rigidity as the probe portion 5 (module) is improved and the sealing property is also improved.

In the sectional structure of the probe portion 5 in the linear state shown in FIG. 13A, the sheath member 15 has a circular shape. However, when the probe portion 5 is bent, the sheath member 15 is deformed so as to become flattened, and there may be a thinned portion where the sheath member 15 is thinner than the original thickness of the optical fiber braided portion 14 provided therein. This thinned deformed portion directly applies an external force to the optical fiber braided portion 14, and may deform or damage the optical fiber braided portion 14. In addition, rotation or movement of the probe portion 5 around or along the longitudinal axis or movement of the optical fiber 13 in the longitudinal axis direction is likely to occur.

Therefore, the maximum curvature (or minimum bending radius) of the probe portion 5 is defined. In this case, at the time of bending at the maximum curvature, a plurality of bundled fibers 13 should not be pressed by an inner surface of the sheath member. For this purpose, the probe portion 5 is formed in consideration of the gap length between the sheath member and the fibers so that the bending radius of the probe portion 5 does not fall below the minimum bending radius. By taking such a gap length, as shown in FIG. 13B, even if the probe portion is deformed so as to become flattened, a state in which a gap is formed is maintained. Therefore, problems caused by flattening can be avoided. Although the gap is treated as a space in the above description, the gap may be filled with an elastic member or a shock absorbing member, which is soft and highly elastic and covers the optical fiber braided portion 14 of the probe portion 5.

(First Example of Braided Structure with Core Member)

With reference to FIG. 14A, a first example of a braided structure with a core member will be described. In the following embodiments, including this embodiment, a structure obtained by winding a small diameter bending member around a core member is referred to as "a braided structure with a core." Also, a structure obtained by braiding small diameter bending members into a triple braid or the like without a core member is simply referred to as "a braided structure."

Further, the optical fiber 13, which is a small diameter bending member, is regarded as a unit of bundle by bundling one or two or more, and two or more bundles are regarded as a set. Here, even a single small diameter bending member is regarded as one bundle. Therefore, for example, two small diameter bending members are regarded as one bundle, and two bundles as one set. In this way, when forming a braided structure with two sets of small diameter bending members, the braided structure is configured of four small diameter bending members. In the example using the optical fibers 13 as the small diameter bending members, if the number of the optical fibers 13 is less than the number (the number of sets) required for braiding, one or more small diameter bending members of a different kind may be used as a substitute to supplement the shortage. As a substitute small diameter bending member, for example, an optical fiber element having the same diameter as the optical fiber 13 may be used as a dummy as described later. Since this dummy optical fiber does not actually guide a light beam, it need not be provided with a detection target portion 16. In the braided structure with or without a core member of this embodiment, when a plurality of small diameter bending members are regarded as one bundle and a set is composed of a plurality of bundles, the small diameter bending members in the respective bundles or sets are equal in number. By equalizing the number, it is preferable that the change in diameter of the probe portion 5 be uniform when braided, so that a load can be uniformly applied to all parts of the probe portion 5. However, it is also possible to braid bundles of different numbers of small diameter bending members by specially setting the cycle (winding interval) when winding the bundles around the core member 12. In particular, a kind and a cross-sectional structure of the braided structure formed of a plurality of optical fibers or dummy optical fibers can be selected to meet the purpose. For example, if the purpose is a mechanical improvement, such as an increase in braid strength or flexibility or reliability of bending, or a reduction of time of braiding work, the combination of the number of optical fibers and the number of dummy fibers is adjusted. If the purpose is reinforcement of strength, improvement of curvature, diameter reduction, etc., the number of dummy fibers may be selected.

In the first example shown in FIG. 14A, a braided structure of optical fibers 21a, 21b, 22a, and 22b in two sets (first and second sets), each consisting of two bundles provided with the detection target portions 16 will be described.

First, the optical fiber 21a of the first set is spirally wound clockwise (CW) around the core member 12 along the longitudinal direction, and the optical fiber 21b is spirally wound counterclockwise (CCW) in the same manner. The optical fibers 21a and 21b are braided to cross at a plurality of intersecting points X1 in a cycle (=pitch) p of intersecting every half cycle (half turn), that is, every 180 degrees.

Next, the optical fiber 22a of the second set is spirally wound clockwise (CW) around the core member 12, and the optical fiber 22b is spirally wound counterclockwise (CCW) in the same manner. The optical fibers 22a and 2bb are braided to cross at a plurality of intersecting points X2 in a cycle (p/2 pitch) of intersecting every half cycle, that is, every 180 degrees. At this time, the intersecting point X1 of the first set of optical fibers 21a and 21b and the intersecting point X2 of the second set of optical fibers 22a and 22 b are arranged in a position opposite to each other across the center of the core member 12 on the same circumference. In other words, when the intersecting point X1 exists on the front side of the core member 12 shown in FIG. 14A, the intersecting point X2 exists on the back side of the core member 12. When forming a long braided structure, this periodic structure is advantageous in arithmetic processing of shape detection. The order in which the optical fibers 21a, 21b, 22a, 22b are wound around the core member 12 is not limited to the above-described order, and may be changed as appropriate.

(Second Example of Braided Structure with Core Member)

With reference to FIG. 14B, a second example of a braided structure with a core member will be described. This example is a braided structure similar to the first example of the braided structure described above, that is, the braided structure of optical fibers 21a, 21b, 22a, and 22b in two sets (first and second sets), each consisting of two bundles.

In the second example of the braided structure, the optical fibers 21a and the optical fiber 22a of the first set and the second set are spirally wound clockwise (CW) around the core member 12 along the longitudinal direction at an interval of a p/4 pitch. The optical fibers 21b and the optical fiber 22b of the first set and the second set are spirally wound counterclockwise (CCW) around the core member 12 at an interval of a p/4 pitch, so that the optical fibers of each set intersect every half cycle.

At this time, the intersecting point X1 of the first set of optical fibers 21a and 21b and the intersecting point X2 of the second set of optical fibers 22a and 22b are arranged with a positional deviation of the p/4 pitch. The amount of deviation in this winding may be appropriately changed depending on ease of manufacture, a difference in shape, size, function, and the like.

(Third Example of Braided Structure with Core Member)

With reference to FIG. 14C, a third example of a braided structure with a core member will be described. This example is a braided structure formed of a set of two bundles: optical fibers 25a and 25b; and optical fibers 25c and 25d. In this example, it is assumed that each of the four optical fibers is provided with the detection target portion 16 for use in shape detection. However, as long as the number of bundles and the number of sets are the same, there is no particular limitation. In this example, it is also possible to use three optical fibers provided with detection target portions in combination with one dummy optical fiber (to be described later) of the same diameter and not provided with a detection target portion.

In this third example of the braided structure, the optical fibers 25a and 25b together are spirally wound clockwise (CW) around the core member 12 in the longitudinal direction. Similarly, the optical fibers 25c and the optical fibers 25d of the first set and the second set are spirally wound counterclockwise (CCW) around the core member 12 and braided in the same cycle (=pitch) p so as to intersect every half cycle. At this time, the intersecting point X1 of the bundle of the optical fibers 25a and 25b and the intersecting point X2 of the bundle of the optical fibers 25c and 25d coincide. Each of the bundle of the optical fibers 25a and 25b and the bundle of the optical fibers 25c and 25d may be stranded.

The braided structures shown in 14A, 14B, and 14C have the same braided pattern (structure) except that a plurality of small diameter bending members braided on the core member 12 are arranged in a mirror-image arrangement of reverse winding.

Further, in the braided structures shown in 14A, 14B, and 14C, "2" of the number of bundles of one set of small diameter bending members is the minimum number to achieve a braided structure having an intersection. Assuming that the number of bundles included in one set is m ($\geq 2$) and the number of bundles that intersect at once at the same position is n ($\geq 2$), the number of intersections per cycle p is $_mC_n$.

If the interval L between the intersecting positions is constant, then $p = {_mC_n} \cdot L$. Since the minimum value of L is considered to be almost constant irrespective of the braided structure, the length of one cycle p becomes smaller as the value of $_mC_n$ is smaller. The combination of m and n that minimizes $_mC_n$ is m=n=2, and $_mC_n=1$. At this time, $p = {_mC_n} \cdot L = L$.

From the above, in the braided structure with the core member, the braided structure by two bundles may minimize a cycle (=pitch) p.

Figure 15:
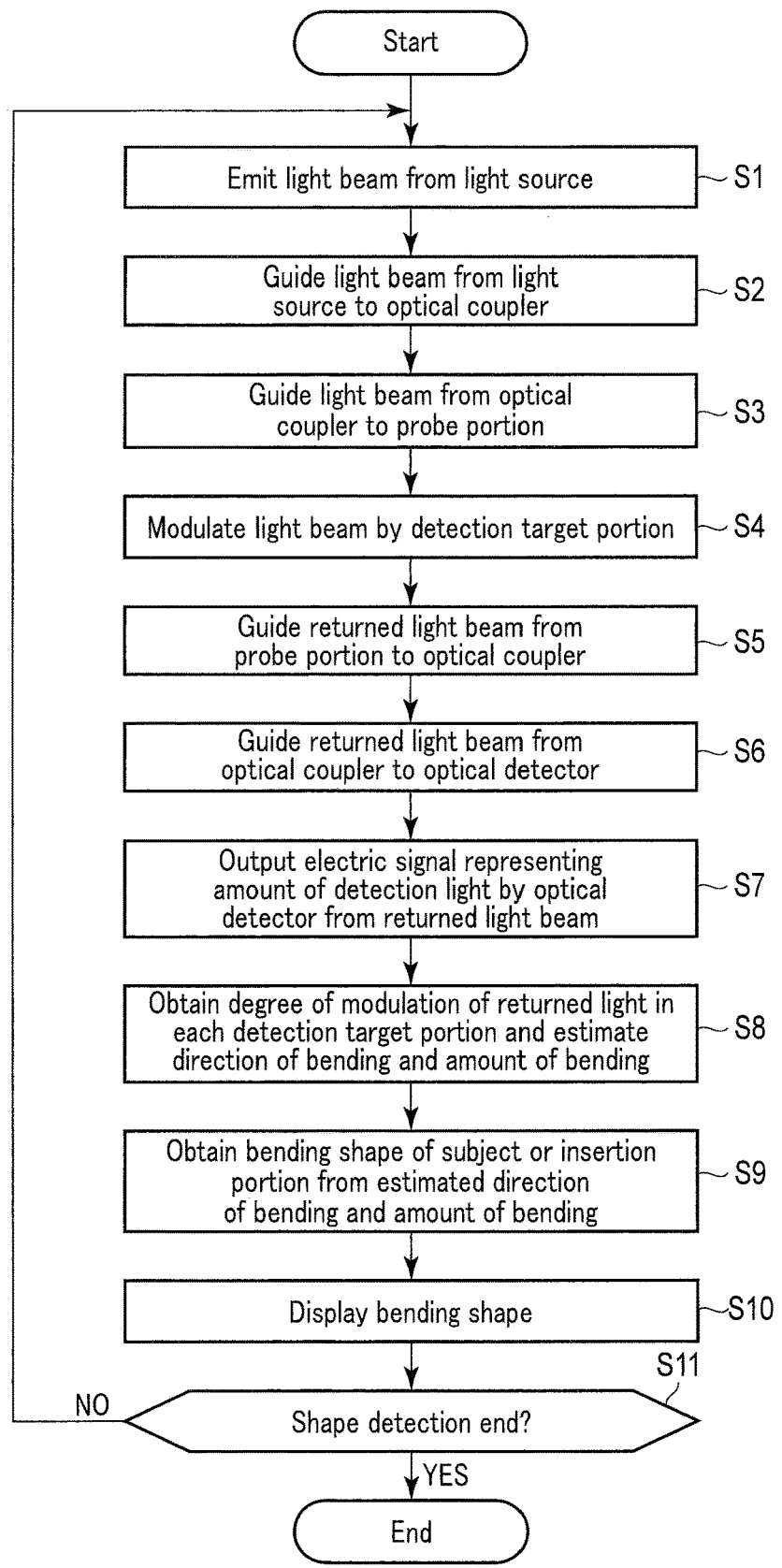
FIG. 15 is a flowchart for explaining a procedure of generating and outputting a bending shape of a subject by the shape sensor system of the embodiment.

Next, referring to FIGS. 1A and 7 and the flowchart of FIG. 15, procedures for generation and output (display) of the bending shape of the subject by the shape sensor system 1 of the present embodiment, using the fiber sensors as the shape sensor, will be described.

First, the light source 2 is driven to emit a light beam which is a detection light having a desired wavelength characteristic (step S1). The light beam from the light source 2 is guided to the optical coupler 4 of the optical connection unit 3 through the light guide path (step S2). Furthermore, the light beam is guided from the optical coupler 4 to the optical fiber 13 of the probe portion 5 through the light guide path (step S3). The light beam is modulated (wavelength fluctuation, light amount fluctuation or the like) by the detection target portion 16 provided in the optical fiber 13 (step S4).

Next, the returned light beam from the probe portion 5 is guided through the light guide path so as to return to the optical coupler 4 (step S5). From the optical coupler 4, the returned light beam is guided to the optical detector 7 through the light guide path (step S6). The optical detector 7 detects each returned light beam modulated by each detection target portion 16 (step S7).

The degree of modulation of the returned light beam detected by each detection target portion 16 is obtained, and the bending direction or bending amount in the vicinity of each detection target portion 16 is estimated (step S8). The bending shape of the subject 6 or the insertion portion 9 is obtained from these estimated bending direction and bending amount in the vicinity of each detection target portion 16. The obtained bending shape of the subject 6 or the insertion portion 9 is output or displayed (step S10). Then, it is determined whether or not to continue a shape detection (step S11). If the shape detection is to be continued (YES), the process returns to step S1. If the shape detection is not to be continued (NO), a series of the shape detection is ended.

Next, with reference to FIG. 16A and FIG. 16B, structural examples of a plurality of holding portions formed in and in the vicinity of the small diameter bending members of the braid structure described above and the detection target portions will be described.

In the probe portion 5 of the present embodiment, the optical fibers 13, which are small diameter bending members, need to be held and fixed so that the detection target portion 16 may not move or twist, when twisting force acts on the optical fiber 13 as the probe portion 5 is bent. Portions of the optical fiber 13 to be held may be an overlapping portion between the optical fibers 13, an overlapping portion between the detection target portions 16, a portion between the optical fiber 13 and the core member 12, a portion between the optical fiber 13 and the sheath member 15, etc.

FIG. 16A shows a first structural example for holding the optical fibers 13. The first structural example for holding includes a holding portion 41 which bonds, with an adhesive, the central portions of the detection target portions 16 to the core member 12 individually, and a holding portion 42 which bonds, with an adhesive, part of the optical fibers 13 in the vicinity of the detection target portions 16 to the core member 12.

FIG. 16B shows a second structural example for holding the optical fibers 13. The second structural example includes a holding portion 43 which bonds, with an adhesive, an intersecting portion of the optical fibers to the core member 12, and a holding portion 44 which bonds, with an adhesive, an intersecting portion of the detection target portions 16 to the core member 12.

With the holding portions 41 to 44, the optical fibers 13 as the small diameter bending members and the detection target portions 16 are held to the core member 12. Therefore, even if the probe portion 5 is bent, the detection target portions 16 do not move or twist relative to the probe portion 5. Furthermore, the distal end portion 18 of the probe portion 5 can also fix the probe portion 5 to the insertion portion 9 or the subject 6. Therefore, no displacement or movement of the detection target portion 16 relative to the insertion portion 9 or the subject 6 occurs, and accurate position detection can be performed.

Next, referring to FIGS. 17A and 17B, formation of the holding portion, when the pitch (pitch) p of the braid of the optical fibers 13 is shorter than that of the holding portion shown in FIGS. 16A and 16B, will be described.

As shown in FIG. 17A, a plurality of holding portions that bonds to the core member 12 are provided for every two bundles at a certain interval (pitch) pc of a cycle (interval) longer than the pitch p. In this structure, holding portions 43, 44, 45 are provided, which bond the optical fibers 13 to the core member 12 at an intersecting portion x1 (x2) of the optical fibers 13 of adjacent sets, an intersecting portion y1 of the detection target portions 16, and an intersecting portion y2 of the optical fibers 13 in the vicinity of the detection target portions 16.

Figure 17B:
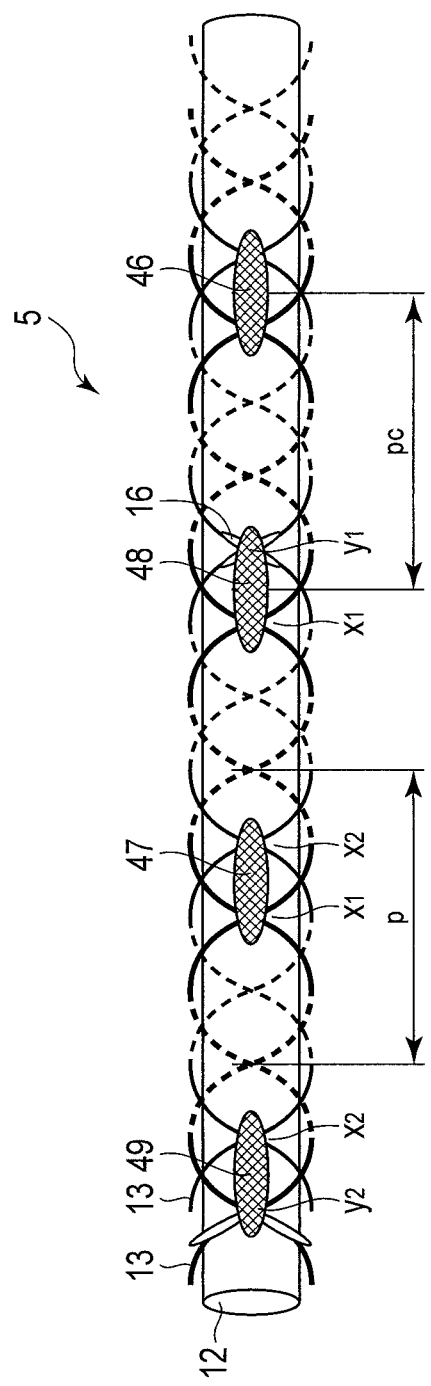
FIG. 17B is a view showing a structural example in which a holding portion that bonds optical fibers to a core member is provided for every four bundles in a cycle that is the same as or longer than a pitch p.

As shown in FIG. 17B, a plurality of holding portions that bond to the core member 12 are provided for every four bundles at a certain interval (pitch) pc of a cycle (interval) equal to or longer than the pitch p. In this structure, a holding portion 47 is provided, which bonds intersecting portions x1 and x2 of the optical fibers 13 to the core member 12

A holding portion 48 is provided, which bonds the intersecting portion x1 of the optical fibers 13 and intersecting portions y1 of the detection target portions 16 to the core member 12. Furthermore, a holding portion 49 is provided, which bonds the intersecting portions x2 of the optical fibers 13 and an intersecting portion y2 of the optical fibers 13 in the vicinity of the detection target portions 16 to the core member 12. In these holding portions, the relationship between the braid cycle p of the optical fibers 13 and the holding pitch pc of the optical fiber 13 is pc≥p.

Figure 18:
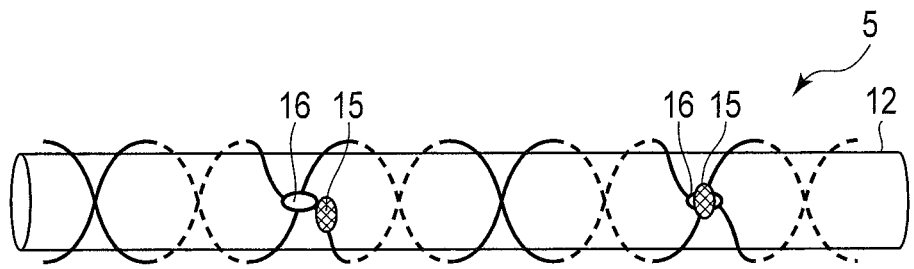
FIG. 18 is a view showing an example of arrangement of detection target portions in a braided structure with a core member.

With reference to FIG. 18, an example of arrangement of the detection target portions 16 will be described.

In the arrangement example of the detection target portions 16 described above (e.g., FIG. 16A), since the optical fibers 13 are braided to spirally wind around the core member, the detection target portions 16 are arranged obliquely to the longitudinal direction of the core member 12. In the arrangement example shown in FIG. 18, the detection target portions 16 are fixed by holding portions 50 so as to be parallel to the longitudinal direction of the probe portion 5. With this arrangement, the bending direction detected by the detection target portions 16 and the bending shape of the probe portion 5 coincide. Therefore, by arranging the detection target portions 16 in parallel with the longitudinal direction, an accurate bending state can be easily detected without correction, unlike in the case of arranging the detection target portions 16 obliquely, in which case the detected direction needs to be corrected.

Such an arrangement may be realized by arranging the optical fibers in parallel with the longitudinal direction of the probe only in the vicinity of the detection target portions 16, or by making the cycle of braiding near the detection target portions 16 longer. In such an arrangement, it is possible to obtain characteristics of the shape sensor equivalent to those in parallel or almost parallel arrangement.

Next, the direction of the detection target portions 16 relative to the center of the core member 12 will be described.

Fundamentally, the detection target portions 16 detect a bending in a specific direction. The detection target portions 16 are braided around the core member 12 together with the optical fibers 13, and each of the detection target portions 16 is spirally arranged with respect to the core member 12. Therefore, when the direction of the detection target portions 16 with respect to the center of the core member 12 is changed, the amount of bending and the bending direction in the vicinity of the detection target portion, which is detected as a reference in the probe portion 5 in a straight state, are changed.

Therefore, if the direction of the detection target portions 16 with respect to the center of the core member 12 can be aligned, it is possible to suppress variations in the detection characteristics of the respective detection target portions 16 and to obtain characteristics having a similar tendency. Furthermore, by specifying the direction with respect to the center of the core member according to the bending characteristic of the fiber sensor, it is possible to improve the dynamic range, linearity, detection accuracy, and the like of the bending characteristic.

(Dummy Optical Fiber)

Next, referring to FIG. 19, a dummy small diameter bending member or optical fiber used as a substitute for a small diameter bending member will be described.

Generally, the number of optical fibers for detection provided with the detection target portions 16 as shown in FIG. 16A is determined by the number of detection target portions 16 provided at the portion where the amount of bending is desired to be measured and the physical restrictions at the insertion portion (the number of detectors, the space to be arranged, etc.) On the other hand, the number of small diameter bending members used for braiding is a specific number, for example, multiples of 2 or multiples of 3 depending on the braided structure. At that time, the following formula (1) needs to be satisfied.

Number of optical fibers for detection≤number of small diameter bending members used for braiding    (1)

As described above, as a countermeasure against the case where the number of the small diameter bending members necessary for braiding is larger than the number of the detection optical fibers 13 used for detection, one or more dummy small diameter bending members, i.e., dummy optical fibers in this example, may be used as a substitute to supplement the shortage.

In the case of using the optical fibers 13 as the small diameter bending members, if the number of the optical fibers 13 is less than the number (the number of sets) required for braiding, one or more small diameter bending members of a different kind may be used as a substitute to supplement the shortage. As a substitute small diameter bending member, for example, an optical fiber having the same diameter as the optical fiber 13 and having no detection target portion 16 may be used as a dummy.

Figure 19:
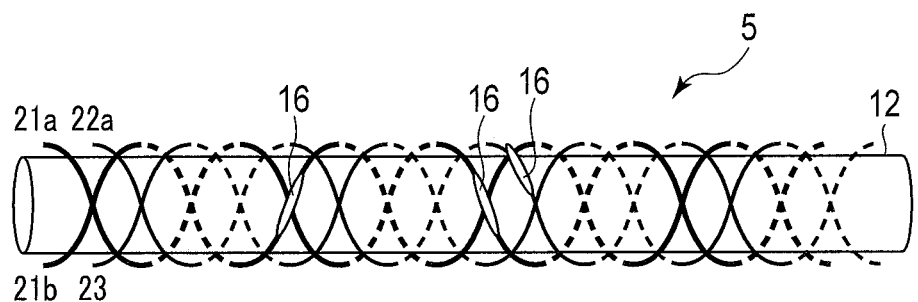
FIG. 19 is a view showing a structural example of a braided structure with a core member including a dummy small diameter bending member.

For example, the braided structure shown in FIG. 19 is equivalent to the structure shown in FIG. 14A, in which two sets (first and second sets), each consisting of two bundles, are spirally wound around the core member. Specifically, the first set includes optical fibers 21a and 21b provided with the detection target portions 16, and the second set includes an optical fiber 22a and a dummy optical fiber 23.

The dummy optical fiber 23 is formed of a material that is equivalent to or higher in durability than the optical fibers 21a, 21b, and 22a for detection, so as not to affect the detection target portions 16 of the other optical fibers. This dummy optical fiber 23 is an optical fiber element which is formed of the same material and has the same diameter as that of the optical fiber for detection, and through which a light beam for detection is not guided. Therefore, the dummy optical fiber 23 need not be provided with a detection target portion 16.

Figure 20A:
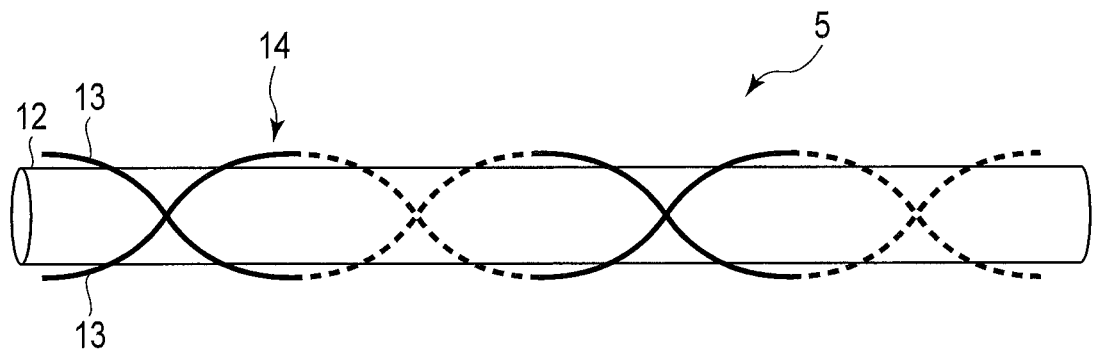
FIG. 20A is a view showing a structural example of a braided structure with a core member in a state where a probe portion is straight.

Next, with reference to FIG. 20A and FIG. 20B, the length of an optical fiber in the probe portion 5 of the braided structure in the straight and bent states will be described. FIG. 20A shows the braided structure in which the probe portion is straight, and FIG. 20B shows the braided structure in which the probe portion is bent.

It is assumed that the optical fiber 13, which is a braided small diameter bending member, is wound around the core member at a position separated by a radius r from the center of the core member. In disregard of the influence of the intersecting portion, the length l of the optical fiber per cycle p is expressed by $$l=\sqrt{p^2+(2\pi r)^2}.$$

Figure 20B:
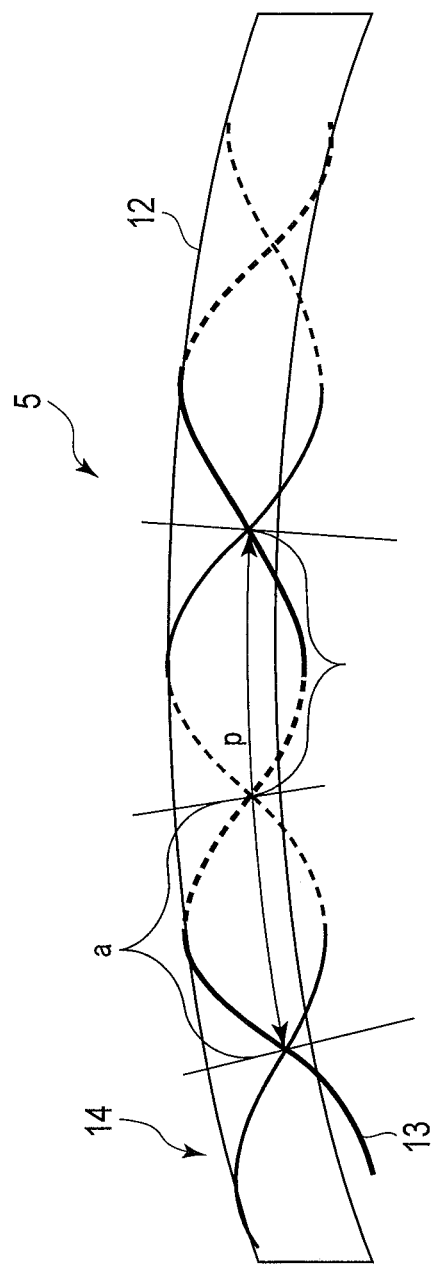
FIG. 20B is a view showing a structural example of a braided structure with a core member in a state where a probe portion is bent.

In FIG. 20B, when the optical fiber braided portion 14 is bent, a portion in an outer side of the bent optical fiber 13 is denoted by a, and a portion in an inner side is denoted by b. Before bending, both the part a and the part b have a length of ½p. When the probe portion 5 is bent, the part a becomes long because it is located on the outer side, and the part b is shortened because it is located on the inner side. However, the length of the optical fiber 13 per one cycle p does not substantially change and remains as p because the amount of extension of the part a and the amount of contraction of the part b are substantially equal. Thus, the fact that the length of the optical fiber 13 per cycle p does not change applies, whichever direction the optical fiber 13 is bent or even in a case where the optical fiber is bent at a plurality of positions.

Therefore, regardless of the presence or absence of a bending, the length of the optical fiber 13 per cycle p does not change. Since this length is not changed, the optical fiber 13 can be fixed at a position with a periodic interval (length); accordingly, it is possible to hold (fix) the optical fiber 13 at a plurality of positions. At this time, the holding (fixing) interval may be equal to or longer than one cycle p. Conversely, if the interval is less than one cycle p, the function of adjusting the length of the optical fiber 13 per cycle p may not work.

In addition, the value of the braiding cycle (pitch) p affects whether the probe portion 5 can maintain a stable shape regardless of how much the probe portion 5 is bent. That is, when the bending amount is large, it is necessary to reduce the braiding pitch p, and when the bending amount is small, the braiding pitch may be increased.

On the other hand, when the braiding pitch is small and the vicinity of the detection target portions is largely twisted, the amount of change in the detection signal decreases and the detection sensitivity may decrease. Also, if the braiding pitch is increased, the small diameter bending members become almost straight, and a detection result can be close to the detection result in the non-braided state.

Figure 20C:
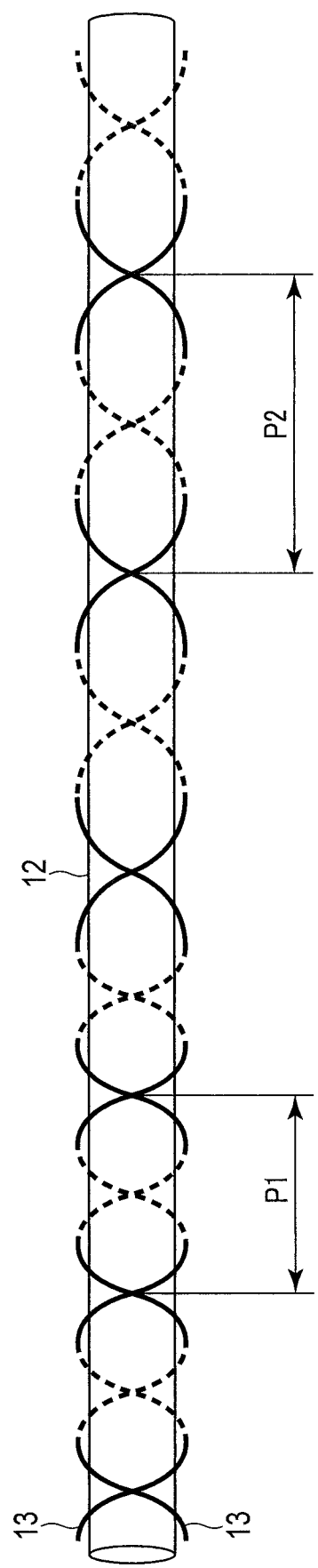
FIG. 20C is a view showing a structural example in which two optical fibers are alternately braided with different pitches.
Figure 20D:
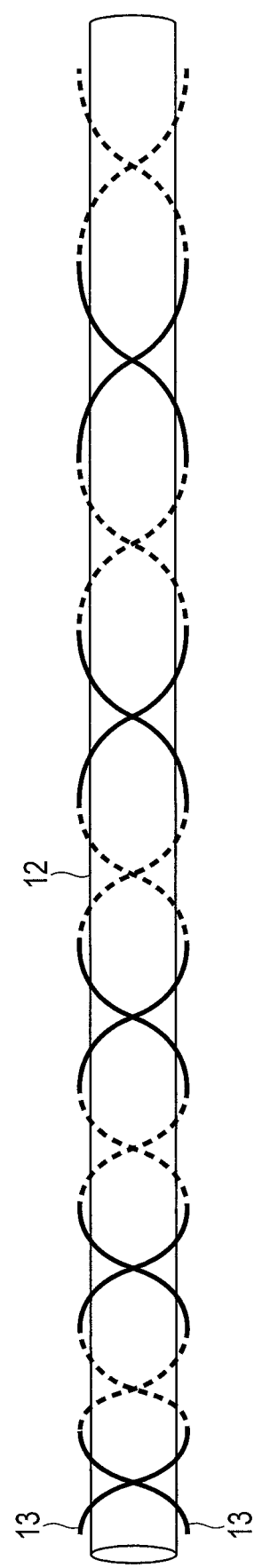
FIG. 20D is a view showing a structural example in which two optical fibers are braided such that the pitch becomes gradually larger from the left to the right.

In consideration of the above, it is necessary to select an appropriate value as the value of the braiding cycle (pitch) p in accordance with the maximum amount of bending. If the value of the cycle (pitch) p is determined from the maximum amount of bending of the probe as a whole, the bending members can be braided at a constant bending pitch, which facilitates manufacturing. On the other hand, when the amount of bending of a specific part of the probe portion is large or the amount of bending becomes larger when approaching the tip, it may be effective to use a plurality of braiding cycles (pitches) p, or to gradually change the cycle, as shown in FIGS. 20C and 20D. FIG. 20C shows a structural example, in which the two optical fibers 13 are alternately braided with different pitches p1 and p2 (p1<p2). FIG. 20D shows a structural example, in which the two optical fibers 13 are braided such that the pitch becomes gradually larger from the left to the right.

The shape sensor system 1 according to the first embodiment described above has the following effects and advantages.

The probe portion 5 has the braided structure, in which sets of small diameter bending members including one or more optical fibers 13 provided with the detection target portions 16, each set consisting of a plurality of bundles of small diameter bending members, are spirally wound around the core member 12 so as to intersect. The probe portion 5 having the braided structure is unlikely to cause the optical fibers 13 to move in the longitudinal direction or to rotate around the probe irrespective of the diameter of the probe portion 5 or the arrangement of the optical fibers 13 in the probe. Therefore, even if the number of optical fibers 13 for detection increases, a shape sensor with high accuracy and high reliability can be provided. Furthermore, by adopting the braided structure, the function of adjusting the fiber length within the braiding cycle can be fulfilled, and the optical fiber 13 disposed at a position deviated from the central axis of the probe portion 5 can be held or fixed at a plurality of positions.

In the braided structure, the two bundles or more of small diameter bending members are spirally wound around the core member 12 of the probe portion 5 in the longitudinal direction at a substantially constant cycle. Therefore, the positions of the detection target portions or the length of the optical fibers necessary for braiding can be easily specified, which facilitates manufacturing.

Furthermore, the braided structures have a simple structure of the same braided pattern (structure) except for a cycle shift and a mirror-image arrangement, which facilitates manufacturing. In addition, the positions of the detection target portions 16 or the length of the optical fibers 13 necessary for braiding can be easily specified.

Since the core member 12 having high rigidity (torsion, expansion and contraction) is arranged substantially in parallel with the probe portion 5, the rigidity of the probe portion 5 is improved and the probe portion 5 becomes resistant against the circumferential rotation and expansion and contraction. Therefore, a detection error in the bending direction is unlikely to occur, and buckling due to breakage or compression of the optical fiber 13 due to pulling is unlikely to occur. Therefore, higher precision and higher reliability are obtained as compared with a probe portion comprising only the optical fibers.

According to the braided structure with the core member of the present embodiment, the structure, in which one set consists of two bundles of small bending members, can minimize the braiding pitch. Therefore, the function of adjusting the length of the optical fiber 13 with respect to the local bending is improved, and it is possible to address the bending with the largest curvature, that is, the smallest radius of curvature, using the same material. Further, since the braiding pitch is the smallest, the fixing interval of the optical fibers 13, which has to be larger than the braiding pitch, can be minimized.

Since the optical fibers 13 are fixed to the core member 12 in the vicinity of the detection target portions 16, the direction and position of the detection target portions 16 are less likely to deviate from the core member. By using the core member 12 having high rigidity with respect to twisting and expansion and contraction, twisting of the portion related to the shape detection of the probe portion 5 is unlikely to occur, and detection accuracy improves. In addition, fixation in the vicinity of the detection target portions 16 is most effective at the minimum positions necessary to make the direction and position of the detection target portions 16 less likely to deviate from the core member. Therefore, the fixation mentioned above is the most efficient in terms of design and manufacturing.

Since the optical fibers 13 for detection in the vicinities of the detection target portions 16 are spirally fixed to the core member 12 at a predetermined pitch, the direction and position of the detection target portions 16 are less likely to deviate from the core member. By using a core member having high rigidity related to twisting and expansion and contraction, twisting of the portion related to the shape detection of the probe portion 5 is unlikely to occur. As a result, it is possible to improve detection accuracy or to fix the core member to the probe portion only at both ends or only one end of the probe portion. In addition, fixation of the optical fibers 13 at a predetermined pitch does not require consideration of the position and positional deviation of the detection target portions 16, which facilitates designing and manufacturing. The optical fibers 13 may be fixed to a limited range of the core member. Alternatively, it is possible to fix the detection target portions 16 to the core member 12 in one range of the probe in one configuration, and to fix the optical fibers 13 to the core member 12 at a predetermined pitch irrespective of the position of the detection target portions 16 in another range of the probe in another configuration. Furthermore, by overlapping the aforementioned two configurations, advantages of both configurations can be utilized. In addition, since the detection target portions 16 are arranged at a predetermined pitch, they can be used as both holding and fixing pitches in common. Therefore, designing and manufacturing for holding and fixing becomes simple.

By disposing the detection target portions 16 substantially in parallel with the probe portion 5, the bending shapes of the probe portion 5 and the detection optical fiber 13 substantially coincide in the vicinity of the detection target portions. Therefore, the detection value of the bending shape of the optical fiber 13 at the detection target portion 16 can be used directly as the detection value of the probe portion 5. Furthermore, since the probe portion 5 is not bent but straight, the measurement error can be smaller than that of the detection target portion 16 arranged obliquely with respect to the probe portion 5.

Since the small diameter bending members include the dummy small diameter bending member (the optical fiber having no detection target portion), if the number of optical fibers 13 necessary for detection differs from the number of the small diameter bending members necessary for the braided structure, a desired shape sensor can be provided by adding the dummy small diameter bending member. Further, by using the optical fiber 23 having no detection target portion 16 as a dummy, it is possible to substantially eliminate the difference in mechanical characteristics between the small diameter bending members used for braiding. Thus, a balanced braided structure can be realized.

The probe portion 5 is provided with the sheath member 15 on the outside so as to enclose the small diameter bending members, thereby protecting the optical fiber braided portion. In addition, in the probe portion 5, the optical fiber 13 is reliably held without rotating around the longitudinal axis or moving along the longitudinal direction from an external influence. Also, the probe portion 5 has a structure in which the maximum curvature (or the minimum bending radius) is determined and the cross-sectional shape of the sheath member includes a cross-sectional shape of a bundled small diameter bending members at the time of bending. Thus, it is possible to prevent the optical fiber braided portion from being deformed or broken.

Second Embodiment

Next, a shape sensor system according to a second embodiment will be described with reference to FIGS. 21A and 21B. FIG. 21A is a view showing an example of a braided structure in which optical fibers of small diameter bending members are braided into a triple braid. FIG. 21B is a view conceptually showing a structure of a triple braid of strings. The shape sensor system of the present embodiment is equivalent to the system configuration of the first embodiment described above, and the same reference numerals are used to omit the description of the constituent parts here, and only the characteristic part will be described.

The shape sensor system 1 of the present embodiment is provided with a probe portion 5 having a braided structure using three small diameter bending members, here, the optical fibers 13, without using the core member 12 described above. The structure of the triple braid structure shown in FIG. 21A is the same as those shown in FIGS. 14A, 14B, and 14C described above, and all of the plurality of braided small diameter bending members have a common braiding pattern (structure). In this triple braid structure, the number of small diameter bending members is the smallest number that can provide a braided structure with intersections without a core member.

In the present embodiment, since the core member is not used, it is possible to realize a smaller diameter than the probe portion having the core member. Since the optical fibers are braided at the same pitch, the positions of the detection target portions or the length of the optical fibers necessary for braiding can be easily specified, which facilitates manufacturing.

Next, FIG. 22 is a view showing a braided structure example of a triple braid including a dummy optical fiber in small diameter bending members according to a first modification. This modification is a triple braid structure in which one optical fiber 13 and two dummy optical fibers 23 are braided. As also described above, the dummy optical fibers 23 may be optical fiber elements having the same diameter and not provided with detection target portions 16.

This first modification produces the same effects and advantages as the second embodiment. Furthermore, since the optical fiber elements with no detection target portions are used, the first modification can be realized at a lower cost than the triple braided structure according to the second embodiment.

Next, FIG. 23 is a view showing a structural example of a triple braid of small diameter bending members including a metal strand according to a second modification. FIG. 24 is a view showing a state in which the vicinity of a detection target portion is fixed to the metal strand by adhesion in the second modification In this modification, two optical fibers and a thin metal strand as a dummy small diameter bending member are combined to be braided into a triple braid structure.

In the first modification, a metal strand 24 as the small diameter bending member functions as a substitute for the core member. Therefore, the optical fibers 13 can be easily intertwined with the metal strand, and deviation of the direction and position of the detection target portion 16 is less likely to occur. Further, by using the thin metal strand 24 having a high rigidity as a small diameter bending member, the modification has strength against the twist of the portion related to the shape detection of the probe portion, and does not lower the detection accuracy. In addition, as shown in FIG. 24, the portion where the two optical fibers 23 cross each other in the vicinity of the detection target portion is fixed by a holding portion 52 to the metal wire 24 with an adhesive.

Next, a third modification will be described with reference to FIG. 25. FIG. 25 shows a structure of a braided structure with flat knots in which two small diameter bending members are tied to the core member with the flat knots (a triple braid including the core member).

As shown in FIG. 25, this modification is similar to the braided structure shown in FIG. 14A described above, in which the optical fiber 21a and the optical fiber 21b are wound to intersect every half cycle around a core member 12. In other words, the optical fibers 21a and 21b are braided in a cycle (=pitch) p intersecting at a plurality of intersecting points x1 intersecting every 180 degrees.

Further, besides the triple braided structure, there are also a quadruple braided structure as shown in FIG. 26A and a sextuple braided structure shown in FIG. 26B.

With these quadruple braided structure 26 and sextuple braided structure 27 also, even when the number of small diameter bending members necessary for braiding is insufficient, a desired braided structure can be obtained by adding a dummy small diameter bending member (an optical fiber element with no detection target portion or a thin metal wire).

Further, since a braid of a predetermined length is obtainable, the detection target portions of the optical fibers for detection can be arranged at a predetermined pitch, and the detection target portions can also be arranged at a desired position of the probe portion. In addition, since the modification is a braided structure, there is no need to take the positional deviation of the detection target portions into consideration, the detection accuracy is improved, and designing and manufacturing are facilitated.

The shape sensor system of the present invention described above includes the following effects and advantages.

First, when the probe portion of the shape sensor is bent, movement in the longitudinal direction and rotation around the probe are unlikely to occur in the optical fiber regardless of the thickness of the probe portion and the arrangement of the optical fibers in the probe. Therefore, even when the number of detection fibers increases, a shape sensor with high accuracy and high reliability can be provided. Also, by adopting a braided structure with a core member or a braided structure without a core member, the function of adjusting the fiber length within the braiding cycle is performed. Accordingly, the optical fibers arranged at a position deviated from the central axis of the probe portion can be held and fixed at a plurality of places.

Second, the braided structure has a constant cycle at least within a predetermined range, thereby facilitating the manufacturing process. In addition, the positions of the detection target portions or the length of the optical fibers necessary for braiding can be easily specified. Further, by adopting a simple structure using a common braiding pattern, manufacturing is particularly facilitated. In addition, the positions of the detection target portions or the length of the optical fibers necessary for braiding can be easily specified.

Third, by using a highly rigid core member arranged almost parallel to the probe portion, the rigidity of the probe portion improves, so that the probe portion becomes resistant against the rotation and expansion or contraction around the probe portion in the circumferential direction. Therefore, detection error in the bending direction hardly occurs. Also, breakage of the optical fiber due to pulling or buckling of the optical fiber due to compression is unlikely to occur. Therefore, the probe portion of the present invention is higher in accuracy and in reliability than the probe portion including only optical fibers.

Fourth, in the braided structure with the core member, the structure in which one set consists of two bundles of small diameter bending members can minimize the braiding pitch. Therefore, the function of adjusting the length of the optical fiber with respect to the local bending is improved, and it is possible to address the bending with the largest curvature, that is, the smallest radius of curvature, using the same material. Furthermore, since the braiding pitch is the smallest, the fixing interval of the optical fibers, which has to be larger than the braiding pitch, can be minimized.

Fifth, when the optical fibers for detection in the vicinities of the detection target portions are fixed to the core member, the direction and position of the detection target portion are less likely to deviate from the core member. By using the core member having high rigidity with respect to twisting and expansion and contraction, twisting of the portion related to the shape detection of the probe portion is unlikely to occur, and detection accuracy improves. In addition, fixation in the vicinity of the detection target portions is most effective at the minimum positions necessary to make the direction and position of the detection target portions less likely to deviate from the core member. Therefore, the fixation mentioned above is the most efficient in terms of design and manufacturing.

Sixth, the optical fibers for detection are fixed to the core member at a predetermined pitch longer than the braiding pitch, the direction and position of the detection target portions are less likely to deviate from the core member. By using the core member having high rigidity with respect to twisting and expansion and contraction, twisting of the portion related to the shape detection of the probe portion is unlikely to occur, and detection accuracy improves. In addition, fixation of the optical fibers at a predetermined pitch does not require consideration of the position and positional deviation of the detection target portions, which facilitates designing and manufacturing. The optical fibers may be fixed to a limited range of the core member. Alternatively, the optical fibers may be fixed to a range different from the range where the detection target portions are fixed to the core member. By overlapping the two ranges, advantages of both configurations can be utilized.

Seventh, since the detection target portions are arranged at a predetermined pitch, they can be commonly used as a holding/fixing pitch. Therefore, designing and manufacturing for holding and fixing become simple.

Eighth, disposing the detection target portions substantially in parallel with the probe portion, the bending shapes of the probe portion and the detection optical fiber substantially coincide, in the vicinity of the detection target portions. Therefore, the detection value of the bending shape of the optical fiber at the detection target portion can be used directly as the detection value of the probe portion. Furthermore, since the probe portion is not bent but straight, the measurement error can be smaller than that of the detection target portion arranged obliquely with respect to the probe portion.

Ninth, if the number of optical fibers necessary for detection differs from the number of the small diameter bending members necessary for the braided structure, a desired shape sensor can be provided by adding the dummy small diameter bending member. Further, by using the optical fiber having no detection target portion as a dummy, it is possible to substantially eliminate the difference in mechanical characteristics between the small diameter bending members used for braiding. Thus, a balanced braided structure can be realized.

Tenth, by providing the sheath member, the optical fiber braided portion is protected from the outside. Further, the sheath member can prevent the optical fiber braided portion from rotating around the longitudinal axis or moving in the longitudinal direction due to the influence from the outside, or prevent the optical fiber from moving in the longitudinal direction due to the influence from the outside.

Eleventh, if the maximum curvature (or the minimum bending radius) is determined in the probe portion, it is possible to avoid deformation or damage due to application of force to the optical fiber braided portion during bending by using a sheath member having the cross-sectional shape that includes (that is larger in any direction than) a cross-sectional shape of a bundle of a plurality of small diameter bending members when bending at the maximum curvature. As a result, the rotation of the optical fiber around the longitudinal direction of the probe portion and the movement in the longitudinal direction of the probe portion are less likely to occur.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

The invention claimed is:
1. An endoscope system comprising:
an insertion portion; and
a shape sensor system to detect a bending state or a bending shape of the insertion portion, the shape sensor system comprising:
a shape sensor, the shape sensor comprising:
a probe that has an elongated shape and that is bendable in accordance with a shape of a target portion of the insertion portion; and
a controller comprising hardware, the controller being configured to:
detect a shape of the probe;
detect signals associated with a shape of the insertion portion; and
estimate the shape of the insertion portion from the detected signals,
the probe comprising:
a core having a high rigidity and extending along a longitudinal direction of the probe; and
a plurality of small diameter bending members braided around the core and including one or more small diameter bending probe elements provided with one or more detection target materials from which information is detected to detect the shape of the probe, the small diameter bending members including at least two bundles that are divided into two, wherein one bundle is spirally wound around the core clockwise about a longitudinal direction of the core, the other bundle is spirally wound around the core counterclockwise about the longitudinal direction of the core, and the two bundles are wound at a constant pitch or different pitches and intersect each other at a plurality of portions on the core to form a braided structure that holds the detection target materials so as not to be rotated around the longitudinal direction to fix the small diameter bending members to the core at least near all the detection target materials;
wherein the probe is detachably attached to the insertion portion, the insertion portion including a long bendable channel through which the small diameter bending members are inserted.

2. The endoscope system of claim 1, wherein all of the small diameter bending members braided into the branded structure have the same braided pattern except that some of the small diameter bending members are arranged in a mirror-image arrangement.

3. The endoscope system of claim 1, wherein the small diameter bending members form at least one set, the at least one set comprising two bundles, each of the two bundles comprising at least one small diameter bending member and, each of the two bundles forming the set being wound around the core clockwise and counterclockwise respectively, and braided to intersect every half cycle.

4. The endoscope system of claim 1, wherein the shape sensor comprises fiber sensors including a plurality of optical fibers as the small diameter bending members, each provided with the detection target portions, at least a portion of the small diameter bending members in the braided structure being fixed to the core member by an adhesive.

5. The endoscope system of claim 1, wherein
the shape sensor comprises a fiber sensor including a plurality of optical fibers as the small diameter bending members, each provided with the detection target materials, and
the optical fibers provided with the detection target materials are fixed to the core member at a predetermined pitch.

6. The endoscope system of claim 5, wherein
all the detection target materials are arranged substantially at the predetermined pitch in the longitudinal direction of the probe, and
all the optical fibers provided with the detection target materials are fixed to the core at the predetermined pitch in positions including vicinities of all detection target materials.

7. The endoscope system of claim 4, wherein all the optical fibers provided with the detection target materials are fixed to the core in vicinities of the detection target materials substantially parallel with the core.

8. The endoscope system of claim 6, wherein all the optical fibers provided with the detection target materials are fixed to the core in vicinities of the detection target materials substantially parallel with the core.

9. The endoscope system of claim 1, wherein the small diameter bending members include at least one dummy small diameter bending member similar to the small diameter bending members of the shape sensor for detection.

10. The endoscope system of claim 1, wherein the probe further comprises a sheath arranged to enclose the small diameter bending members from outside.

11. The endoscope system of claim 10, wherein either a maximum curvature or a minimum bending radius is determined in the probe, and
when bending at the maximum curvature, an inner surface of the sheath encircles the small diameter bending members which are bundled in a cross-sectional view.

12. An endoscope system comprising:
an insertion section; and
a shape sensor system to detect a bending state or a bending shape of the insertion portion, the shape sensor system comprising a shape sensor, the shape sensor comprising:
a probe that has an elongated shape and that is bendable in accordance with a shape of a target portion of the insertion portion; and
a controller comprising hardware, the controller being configured to:
detect a shape of the probe portion;
detect signals associated with a shape of the insertion portion; and
estimate the shape of the insertion portion from the detected signals,
the probe comprising:
a core having a high rigidity and extending along a longitudinal direction of the probe; and
a plurality of small diameter bending members braided around the core and including one or more small diameter bending probe elements provided with one or more detection target materials from which information is detected to detect the shape of the probe, the small diameter bending members including at least two bundles that are divided into two, wherein one bundle is spirally wound around the core clockwise about a longitudinal direction of the core, the other bundle is spirally wound around the core counterclockwise about the longitudinal direction of the core, and the two bundles intersect each other at a plurality of portions on the core to form a braided structure that holds the detection target materials so as not to be rotated around the longitudinal direction;

wherein the probe is detachably attached to the insertion portion, the insertion portion including a long bendable channel through which the small diameter bending members are inserted.

13. A shape sensor system to detect a bending state or a bending shape of a subject, the shape sensor system comprising:

a shape sensor, the shape sensor comprising:
a probe that has an elongated shape and that is bendable in accordance with a shape of a target portion of the subject; and
a controller comprising hardware, the controller being configured to:
detect a shape of the probe;
detect signals associated with a shape of the subject; and
estimate the shape of the subject from the detected signals,
the probe comprising:
a core having a high rigidity and extending along a longitudinal direction of the probe; and
a plurality of small diameter bending members braided around the core and including one or more small diameter bending probe elements provided with one or more detection target materials from which information is detected to detect the shape of the probe, the small diameter bending members including at least two bundles that are divided into two, wherein one bundle is spirally wound around the core clockwise about a longitudinal direction of the core, the other bundle is spirally wound around the core counterclockwise about the longitudinal direction of the core, and the two bundles are wound at a constant pitch or different pitches and intersect each other at a plurality of portions on the core to form a braided structure that holds the detection target materials so as not to be rotated around the longitudinal direction to fix the small diameter bending members to the core at least near all the detection target materials;
wherein a value of a braiding pitch p is determined from a maximum amount of bending of the probe as a whole, and the bending members are braided at the determined pitch.

14. A shape sensor system to detect a bending state or a bending shape of a subject, the shape sensor system comprising:

a shape sensor, the shape sensor comprising:
a probe that has an elongated shape and that is bendable in accordance with a shape of a target portion of the subject; and
a controller comprising hardware, the controller being configured to:
detect a shape of the probe;
detect signals associated with a shape of the subject; and
estimate the shape of the subject from the detected signals,
the probe comprising:
a core having a high rigidity and extending along a longitudinal direction of the probe; and
a plurality of small diameter bending members braided around the core and including one or more small diameter bending probe elements provided with one or more detection target materials from which information is detected to detect the shape of the probe, the small diameter bending members including at least two bundles that are divided into two, wherein one bundle is spirally wound around the core clockwise about a longitudinal direction of the core, the other bundle is spirally wound around the core counterclockwise about the longitudinal direction of the core, and the two bundles are wound at a constant pitch or different pitches and intersect each other at a plurality of portions on the core to form a braided structure that holds the detection target materials so as not to be rotated around the longitudinal direction to fix the small diameter bending members to the core at least near all the detection target materials;
wherein when a specific part of the probe is bent at an amount of bending that is larger than in other parts of the probe or that becomes larger when approaching a tip of the probe, the plurality of small diameter bending members comprise a plurality of optical fibers braided around the core at braiding pitches different from one another, or braided at gradually increased pitches.

* * * * *